*(12)* United States Patent
Brooker et al.

*(10)* Patent No.: US 10,591,870 B2
*(45)* Date of Patent: *Mar. 17, 2020

(54) BIREFRINGENT LENS INTERFEROMETER FOR USE IN MICROSCOPY AND OTHER APPLICATIONS

(71) Applicant: CellOptic, Inc., Rockville, MD (US)

(72) Inventors: Gary Brooker, Rockville, MD (US); Nisan Siegel, Silver Spring, MD (US)

(73) Assignee: CellOptic, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,096

(22) Filed: May 5, 2017

(65) Prior Publication Data

US 2017/0242398 A1 Aug. 24, 2017

Related U.S. Application Data

(63) Continuation-in-part of application No. 15/455,863, filed on Mar. 10, 2017, now abandoned, which is a
(Continued)

(51) Int. Cl.
*G03H 1/04* (2006.01)
*G02B 5/30* (2006.01)
(Continued)

(52) U.S. Cl.
CPC ............... *G03H 1/041* (2013.01); *A61B 3/13* (2013.01); *G02B 1/02* (2013.01); *G02B 3/08* (2013.01);
(Continued)

(58) Field of Classification Search
CPC .. G02B 5/3083; G02B 27/283; G02B 5/3016; G02B 27/0172; G02B 1/08;
(Continued)

(56) References Cited

U.S. PATENT DOCUMENTS 3,856,986 A 12/1974 Macovski
4,905,169 A 2/1990 Buican et al.
(Continued)

FOREIGN PATENT DOCUMENTS

WO WO 2014/132781 A1 9/2014
WO WO 2015/168384 A2 11/2015

OTHER PUBLICATIONS

Katz et al. ("Enhanced resolution and throughput of Fresnel incoherent correlation holography (FINCH) using dual diffractive lenses on a spatial light modulator (SLM)" Optics Express, Apr. 9, 2012, vol. 20, No. 8 pp. 9109-9121) (Year: 2012).*
(Continued)

*Primary Examiner* — Jade R Chwasz
(74) *Attorney, Agent, or Firm* — Nixon & Vanderhye, P.C.

(57) ABSTRACT

Techniques to improve image quality in holography utilizing lenses made from materials with non-quantized anisotropic electromagnetic properties, such as birefringent materials, to advantageously split an incoming beam of light into two coincident beams with different focal lengths that interfere with one another and thus create holograms free of electro-optical or pixelated devices are disclosed for microscopy and other applications. The use of thin birefringent lenses and single crystal alpha-BBO lenses are introduced. Corresponding systems, methods and apparatuses are described.

25 Claims, 17 Drawing Sheets

Related U.S. Application Data continuation-in-part of application No. 15/228,386, filed on Aug. 4, 2016, now Pat. No. 10,289,070, which is a continuation-in-part of application No. PCT/US2015/028477, filed on Apr. 30, 2015.

(60) Provisional application No. 62/332,857, filed on May 6, 2016, provisional application No. 61/987,205, filed on May 1, 2014.

(51) Int. Cl.

| | |
|---|---|
| G02B 3/08 | (2006.01) |
| G03H 1/00 | (2006.01) |
| A61B 3/13 | (2006.01) |
| G02B 1/02 | (2006.01) |
| G03H 1/06 | (2006.01) |
| G02B 21/00 | (2006.01) |
| G03H 1/08 | (2006.01) |

(52) U.S. Cl.
CPC ......... *G02B 5/3016* (2013.01); *G02B 5/3083* (2013.01); *G02B 21/0056* (2013.01); *G02B 21/0068* (2013.01); *G03H 1/0005* (2013.01); *G03H 1/0443* (2013.01); *G03H 1/06* (2013.01); *G03H 1/0866* (2013.01); *G03H 2001/005* (2013.01); *G03H 2001/0447* (2013.01); *G03H 2001/0452* (2013.01); *G03H 2222/24* (2013.01); *G03H 2223/17* (2013.01); *G03H 2223/20* (2013.01)

(58) Field of Classification Search
CPC .. G02F 1/13363; G03H 1/0005; G03H 1/041; G03H 1/04; G03H 1/06; G03H 2001/005; G03H 2222/31; G03H 2223/17; G03H 2223/20; G03H 1/0443; G03H 1/0866; G03H 2001/0445
USPC ................... 359/30, 10, 11, 15, 19
See application file for complete search history.

(56) References Cited

U.S. PATENT DOCUMENTS

| | | |
|---|---|---|
| 7,067,784 B1 | 6/2006 | Lowans |
| 7,218,429 B2 | 5/2007 | Batchko |
| 7,826,137 B2 | 11/2010 | Konno et al. |
| 2012/0050832 A1 | 3/2012 | Rosen |
| 2013/0070326 A1* | 3/2013 | Frisken ............... H04L 27/18 359/279 |
| 2013/0083386 A1* | 4/2013 | Harding ............... G01N 21/21 359/240 |
| 2014/0362332 A1 | 12/2014 | Buehler et al. |
| 2016/0011564 A1 | 1/2016 | Tanabe et al. |
| 2017/0052508 A1 | 2/2017 | Brooker |
| 2017/0242398 A1 | 8/2017 | Brooker |

OTHER PUBLICATIONS

Rosen et al. ("FINCH: Fresnel IncoherentCorrelation Hologram", Holography, Research and Technologies, Prof. Joseph Rosen (Ed.), ISBN: 978-953-307-227-2, InTech, «http://www.intechopen.com/books/holography/research-and-technologies/finch-fresnel-incoherent-correlation-hologram» pp. 135-154 (Year: 2011).*
International Search Report and Written Opinion in corresponding PCT Application No. PCT/US2017/031319 dated Jul. 7, 2017.
Lohmann, "Wavefront Reconstruction for Incoherent Objects", Journal of the Optical Society of America, vol. 55, No. 11, Nov. 1, 1965, p. 1555, XP55443774.
Katz et al., "Enhanced Resolution and Throughput of Fresnel Incoherent Correlation Holography (FINCH) Using Dual Diffractive Lenses on a Spatial Light Modulator (SLM", Optics Express, vol. 20, No. 8, Apr. 9, 2012, p. 9109.
Extended European Search Report dated Feb. 9, 2018, in corresponding Application No. 15786627.8.
Brooker et al., "In-line FINCH Super Resolution Digital Holographic Fluorescence Microscopy Using a High Efficiency Transmission Liquid Crystal GRIN Lens," Optics Letters, vol. 38, No. 24, Dec. 15, 2013, pp. 5264-5267; Fig 1-3.
International Preliminary Examination and Written Opinion in related application PCT/US2015/028477 dated Jan. 29, 2017.
JP Office Action dated Oct. 24, 2017 in related Application No. 2017-510440.
Supplementary European Search Report, Application No. EP 17 76 4205 dated Sep. 19, 2019.

* cited by examiner

Classical imaging 912

FINCH imaging With BBO lens 914

BIREFRINGENT LENS INTERFEROMETER FOR USE IN MICROSCOPY AND OTHER APPLICATIONS

CROSS-REFERENCE TO RELATED APPLICATIONS

This application claims the benefit of priority to U.S. Provisional Application Ser. No. 62/332,857 filed on May 6, 2016, and also claims the benefit of priority to and is a continuation-in-part of U.S. patent application Ser. No. 15/455,863 filed on Mar. 10, 2017. U.S. patent application Ser. No. 15/455,863 filed on Mar. 10, 2017 claims the benefit of priority to U.S. Provisional Application Ser. No. 62/306,537 filed on Mar. 10, 2016, and also is a continuation-in-part of U.S. patent application Ser. No. 15/228,386 filed on Aug. 4, 2016. U.S. patent application Ser. No. 15/228,386 claims the benefit of priority to U.S. Provisional Application Ser. No. 62/202,655 filed on Aug. 7, 2015, and is a continuation-in-part of and claims the benefit of PCT Application Serial Number PCT/US2015/028477 filed on Apr. 30, 2015, which claims the benefit of U.S. Provisional Application Ser. No. 61/987,205, filed on May 1, 2014. The entire contents of U.S. Provisional Application Ser. No. 62/332,857, U.S. patent application Ser. No. 15/455,863, U.S. Provisional Application Ser. No. 62/306,537, U.S. patent application Ser. No. 15/228,386, U.S. Provisional Application Ser. No. 62/202,655, PCT Application Serial Number PCT/US2015/028477 and U.S. Provisional Application Ser. No. 61/987,205 are herein incorporated by reference.

GOVERNMENT RIGHTS

This invention was made with U.S. government support under grant R44CA192299 awarded by the National Cancer Institute (NCI). The U.S. government has certain rights in the invention.

FIELD

This disclosure relates to collecting and/or using Fresnel Incoherent Correlation Holography (FINCH) or other holography images generated by use of a birefringent lens or optical element to alter the phase properties of the received light or other electromagnetic radiation.

BACKGROUND

Holograms are records of the interference patterns created by two or more light or other radiation waves. In order for the waves to interfere they must have different phase properties. In current holography methods the waves that are to be interfered are passed through different optical paths that impart different phase properties on each wave. In one class of methods of single-path holography, the waves are commonly given different phase properties by being passed through or reflected off of digitized phase patterns displayed on a spatial light modulator (SLM) or other optical element. In another class of methods for self-interference holography, the waves originate from a single wave and are split by a beam splitter, then reflected off differing mirrors before being recombined in the last part of the beam path and brought to interfere. All of these methods produce holograms that may suffer from significant defects due to slight mismatches in optical path length, quantization errors or undesired diffraction effects of the SLM or other optical element. Apparatuses, systems and/or methods that allow all the waves to pass in the same optical path while receiving different phase properties, without being subject to unnecessary reflections or quantization errors or undesired diffraction effects, would be desirable in the field of holography.

SUMMARY OF EXAMPLE EMBODIMENTS OF THE INVENTION

Accordingly, one object of example embodiments is to provide an apparatus with non-quantized anisotropic electromagnetic properties used to create electromagnetic interference from received electromagnetic radiation, and a method for its use. The anisotropic electromagnetic properties may derive from one or more anisotropic components such as a thin birefringent lens, and may be further adjusted by combination with other materials. The received electromagnetic radiation may be from sources such as x-rays, black body radiation, infrared light, or light of any wavelength from any source, coherent or incoherent. In some embodiments, the received electromagnetic radiation may be from a microscope specimen and/or from a microscope. In the apparatus, the received electromagnetic radiation is then transformed by refraction and/or diffraction into two or more differentially modulated waves propagating in a common path, and the modulated electromagnetic waves create the electromagnetic interference, which can take the form of a Fresnel, Fourier, Fresnel Incoherent Correlation Holography (FINCH), off-axis or other hologram. The interference is recorded by a recording device, and information about the source of the received radiation can be obtained from the interference.

Another object of example embodiments is to provide an apparatus with non-quantized anisotropic electromagnetic properties used to create electromagnetic interference from received electromagnetic radiation, and a method for its use. The anisotropic electromagnetic properties may derive from one or more anisotropic components such as a thin birefringent lens, and may be further adjusted by combination with other materials. The received electromagnetic radiation may be from sources such as x-rays, black body radiation, or light of any wavelength from any source, coherent or incoherent. In some embodiments, the received electromagnetic radiation may be from a microscope specimen and/or from a microscope. In the apparatus, the received electromagnetic radiation is then transformed by refraction and/or diffraction into two or more differentially modulated waves propagating in a common path with programmed differences between the modulations. The modulated electromagnetic waves create the electromagnetic interference, which can take the form of a Fresnel, Fourier, FINCH, off-axis or other hologram. The interference is then used to deliver the programmed information to a subsequent device or object such as a microscope sample or optical recording medium.

Another object of example embodiments is to provide the advantages listed above in configurations that do not require external power sources, allowing interference waves (and holograms) to be obtained in a portable manner.

An example embodiment provides an apparatus with non-quantized anisotropic electromagnetic properties configured to create electromagnetic interference from received electromagnetic radiation. The anisotropic electromagnetic properties of the apparatus may exist independent of external power. The received electromagnetic radiation is transformed by refraction and/or diffraction using at least one thin birefringent lens into two or more differentially modulated waves propagating in a common path such that the modulated electromagnetic waves create the electromagnetic interference. The received electromagnetic radiation may be, for example, fluorescent light, chemiluminescent light, bioluminescent light, infrared light, incoherent light, coherent light, other type of light, x-ray or black body radiation. The anisotropic properties of the apparatus may be derived, for example, from calcite, alpha barium borate, beta barium borate (BBO) or other birefringent materials. In some implementations the anisotropic properties may be derived from liquid crystal material. For example, the liquid crystal material encased in flat or positively or negatively curved non birefringent materials, or may be encased in flat or positively or negatively curved birefringent materials.

The electromagnetic interference created by the apparatus of the example embodiment may be a Fresnel hologram, a Fourier hologram, a FINCH hologram, or an off axis hologram, or other hologram. The received electromagnetic radiation may originate from a microscope and/or microscope specimen, or from a DNA sequencing gel or system. The electromagnetic interference that is created may be recorded, for example, by an image recording device, or by a point source detector. The electromagnetic interference may be used as the excitation pattern in scanning holography, used in an excitation source in a Structured Illumination (SIM) imaging system, or may be used to record data in a holographic storage medium. The received electromagnetic radiation may be coherent or incoherent and may originate from the readout of a holographic data storage medium or any combination of the previous methods. The electromagnetic interference may be interpreted to recover data stored in a holographic storage medium.

The anisotropic electromagnetic properties of the apparatus of the example embodiment may be contained in one or more birefringent lenses. The apparatus may be configured to allow any difference in focal length between the ordinary and extraordinary focal lengths of the combined lens system to be achieved based on choices of the radii of curvature for each surface of the birefringent lens and the focal lengths of any associated standard (also referred to as classical) lenses. Some or all of the radii of curvature of the birefringent lens elements may be infinity. In some implementations, the described lenses are combined in one unit, where the combination means is an optically transmitting substance such as, for example, air or optical cement.

The apparatus of the example embodiment may be configured such that the dispersive properties of the birefringent materials are used to create a multitude of spatially separated wavelength dependent holograms from a broadband electromagnetic radiation source. In such a configuration the spatially separated holograms are directed to separate areas for recording or further use or modification by means of color filters or dispersive prismatic or grating elements. In some implementations, the source of the received electromagnetic radiation may be a human eye Fundus, and the refracted electromagnetic interference may be recorded on a digital camera. In some implementations the source of the received electromagnetic radiation may be a microscope objective lens, and the refracted electromagnetic interference may be used to create classically resolved or optically super-resolved images. In some implementations, other optical devices may be configured to alter the electromagnetic interference to achieve desired spatial, chromatic and temporal characteristics.

Another example embodiment provides a birefringent optical device configured to simultaneously create, from a single source, focused spots at two or more different planes. The focused spots may be used as excitation light in a microscope and are simultaneously focused upon two or more object planes. The birefringent optical device may be a microscope objective. In some implementations, the birefringent optical device may be contained within the microscope objective lens, and may be used to focus laser excitation light into the sample.

Another example embodiment provides a non-quantized birefringent optical device for creating Fresnel, FINCH, Fourier or other holograms from received electromagnetic radiation. The example non-quantized birefringent optical device includes hybrid lenses of birefringent lenses that are created by the combination of birefringent and non-birefringent materials to create polarization sensitive lenses with two or more focal lengths of any specification.

Another example embodiment provides a non-quantized birefringent optical device configured to have any two different focal lengths by combination of lenses of different birefringent materials. The example optical device may be used to create holograms, such as, for example, Fresnel, FINCH, Fourier or other holograms from received electromagnetic radiation. The spacing between the independent focal planes of the lenses (spacing factor) may be varied. The hybrid lenses of birefringent lenses may be created by the combination of birefringent and non-birefringent materials to form polarization sensitive lenses with two or more focal lengths of any specification. In some implementations of the example birefringent optical device, the birefringent optical device may be contained within a microscope objective lens.

Another example embodiment provides a method to create electromagnetic interference from received electromagnetic radiation by using an optical device such as a thin birefringent lens with non-quantized anisotropic electromagnetic properties. The example method includes transforming the received electromagnetic radiation by refraction and/or diffraction into two or more differentially modulated waves propagating in a common path, and creating the electromagnetic interference using the modulated electromagnetic waves. The received electromagnetic radiation may be, for example, fluorescent light, chemiluminescent light, bioluminescent light, incoherent light, coherent light, infrared light, other type of light, x-ray, or black body radiation. The anisotropic properties may be derived from calcite materials, from alpha or beta barium borate materials, or from any material that is anisotropic. In some implementations the anisotropic properties may be derived from liquid crystal material. For example, the liquid crystal material encased in flat or positively or negatively curved non birefringent materials, or may be encased in flat or positively or negatively curved birefringent materials. The created electromagnetic interference may be a hologram such as, for example, a Fresnel hologram, a Fourier hologram, a FINCH hologram, or an off axis hologram. The received electromagnetic radiation may originate from a microscope and/or microscope specimen, or from a DNA sequencing gel or system or any other object that emits or reflects light. The electromagnetic interference that is created may be recorded by an image recording device, or by a point source detector. In some implementations the electromagnetic interference is used as the excitation pattern in scanning holography, as an excitation source in a Structured Illumination (SIM) imaging system, or to record data in a holographic storage medium. In some implementations the received electromagnetic radiation originates from the readout of a holographic data storage medium. The electromagnetic interference may be interpreted to recover data stored in a holographic storage medium.

The example method may operate to use the dispersive properties of the birefringent materials to create a multitude of spatially separated wavelength dependent holograms from a broadband electromagnetic radiation source. In some implementations, the source of the received electromagnetic radiation may be a human eye Fundus, and the refracted electromagnetic interference is recorded on a digital camera. In some implementations, the source may be a microscope objective lens, and the refracted electromagnetic interference is used to create optically super-resolved images Another example embodiment provides a method for simultaneously creating, from a single source, focused spots at two or more different planes using a birefringent optical device. The focused spots may be used as excitation light in a microscope and are simultaneously focused upon two or more object planes. The birefringent lens may be a microscope objective. In some implementations, the birefringent optical device may be contained within the microscope objective lens, and may be used to focus laser excitation light into the sample.

In some implementations, the example method may allow any difference in focal length between the ordinary and extraordinary focal lengths of the combined lens system to be achieved based on choices of the radii of curvature for each surface of the birefringent lens and the focal lengths of any associated standard lenses. Some or all of the radii of curvature of the birefringent elements may be infinity. In some implementations, the described lenses may be combined in one unit, with an optically transmitting substance such as air or optical cement as the combination medium.

Another embodiment provides a method of using non-quantized birefringent optical devices with any two different focal lengths by combination of lenses of different birefringent materials. The method may be used to create holograms such as, for example, Fresnel, FINCH, Fourier or other holograms, from received electromagnetic radiation. The difference between the focal lengths of the lenses may be varied. Hybrid lenses of birefringent lenses may be created by the combination of birefringent and non-birefringent materials to create polarization sensitive lenses with two or more focal lengths of any specification.

Another example embodiment provides a method to use birefringent optical devices incorporating one or more birefringent spherical lenses to form lenses with two or more polarization sensitive focal lengths of any specification.

Another example embodiment provides a birefringent optical device incorporating one or more birefringent spherical lenses to obtain lenses with two or more polarization sensitive focal lengths of any specification.

Another embodiment provides a birefringent device configured to create Fresnel, FINCH, Fourier or other holograms from electromagnetic radiation. The electromagnetic radiation may be light. The birefringent device is composed of a material that is birefringent at optical wavelengths. The birefringent device may be used in conjunction with other optical devices to alter the hologram to achieve desired spatial, chromatic and temporal characteristics. The light beam that is processed by the birefringent device may originate from a microscope specimen. The hologram that is created may be recorded by an image recording device. The light beam originating from the specimen may be fluorescent light whose emission was induced by standard microscopy methods. The light beam originating from the specimen may include fluorescent light whose emission was induced and transmitted in a confocal arrangement, whose emission was induced by multiphoton excitation, or whose emission was induced by nonlinear-optical methods. In some implementations, the light beam originating from the specimen is chemiluminescence light, transmitted light or reflected light. In some embodiments, the light beam that is processed by the birefringent optical device originates from a camera lens, or from a biological sequencing gel. In some embodiments, the electromagnetic radiation is laser light.

In some example embodiments, the birefringent device which is configured to create Fresnel, FINCH, Fourier or other holograms from electromagnetic radiation, which is composed of a material that is birefringent at optical wavelengths, and which may be used in conjunction with other optical devices to alter the hologram to achieve desired spatial, chromatic and temporal characteristics, may be contained within a microscope objective lens. The light beam that is processed by the birefringent device may originate from a microscope specimen. The hologram that is created may be recorded by an image recording device. The birefringent device within the microscope objective lens may be used to focus laser excitation light into the specimen.

Another example embodiment provides a birefringent device configured to create Fresnel, FINCH, Fourier or other holograms from electromagnetic radiation, in which the electromagnetic radiation may be light. The birefringent device is composed of a material that is birefringent at optical wavelengths. The birefringent device may be used in conjunction with other optical devices to alter the hologram to achieve desired spatial, chromatic and temporal characteristics for any given usage modality. The hologram created by the birefringent device may be used as the excitation pattern in scanning holography, providing significant increases in stability over current methods. While scanning holography currently produces the Fresnel hologram used for excitation from a laser beam passed through a modified Michaelson interferometer with two beam paths, some example embodiments us a single beam path through the birefringent device. The single beam path avoids the problems of differing properties of different beam paths, such as relative differences in vibration that can degrade the excitation pattern in conventional scanning holography. In some implementations of the example birefringent device configured to create Fresnel, FINCH, Fourier or other holograms, the hologram may be used to modulate the excitation beam in a Structured Illumination (SIM) imaging system. For example, the birefringent device may be used to impart linear phase difference in the SIM excitation beam instead of spherical phase difference; or a birefringent device with an axicon phase profile may be used; or the outer part of a Fresnel hologram formed form the excitation laser beam, that approximates a linear fringe pattern, may be used.

In some implementations of the example birefringent device configured to be used in conjunction with other optical devices to alter the hologram to achieve desired spatial, chromatic and temporal characteristics, the hologram is used to record data in a holographic storage medium.

In some implementations of the example birefringent device configured to be used in conjunction with other optical devices to alter the hologram to achieve desired spatial, chromatic and temporal characteristics, the light creating the hologram originates from the readout of a holographic data storage medium. The hologram may be interpreted to recover data stored in a holographic storage medium.

In some implementations of the example birefringent device, the birefringent device is configured to use the dispersive properties of the birefringent materials create a multitude of spatially separated wavelength dependent holograms from a broadband electromagnetic radiation source.

The electromagnetic radiation may be coherent, incoherent, fluorescent light, chemiluminescent light, light from a microscope, or light from a DNA sequencing means.

Another example embodiment provides a birefringent optical device configured to focus excitation light into two object planes in a single exposure. The birefringent lens may be a microscope objective.

Another example embodiment provides a birefringent optical device for creating focused images of two differing object planes in a single exposure. The birefringent lens may be a microscope objective.

Another example embodiment provides a birefringent optical devices to create Fresnel, FINCH, Fourier or other holograms from electromagnetic radiation wherein hybrid lenses of birefringent lenses are created by the combination of birefringent and non-birefringent materials to create polarization sensitive lenses with two or more focal lengths of any specification.

Another example embodiment provides a method for holography wherein the choices of the radii of curvature for each surface of the birefringent lens and the focal length of the associated standard lens allow any difference in focal length between the ordinary and extraordinary focal lengths of the combined lens system to be achieved. The described lenses may be combined in one unit. The combining of the lenses may be by means of an optically transmitting substance such as air and/or optical cement.

DETAILED DESCRIPTION

Figure 1:
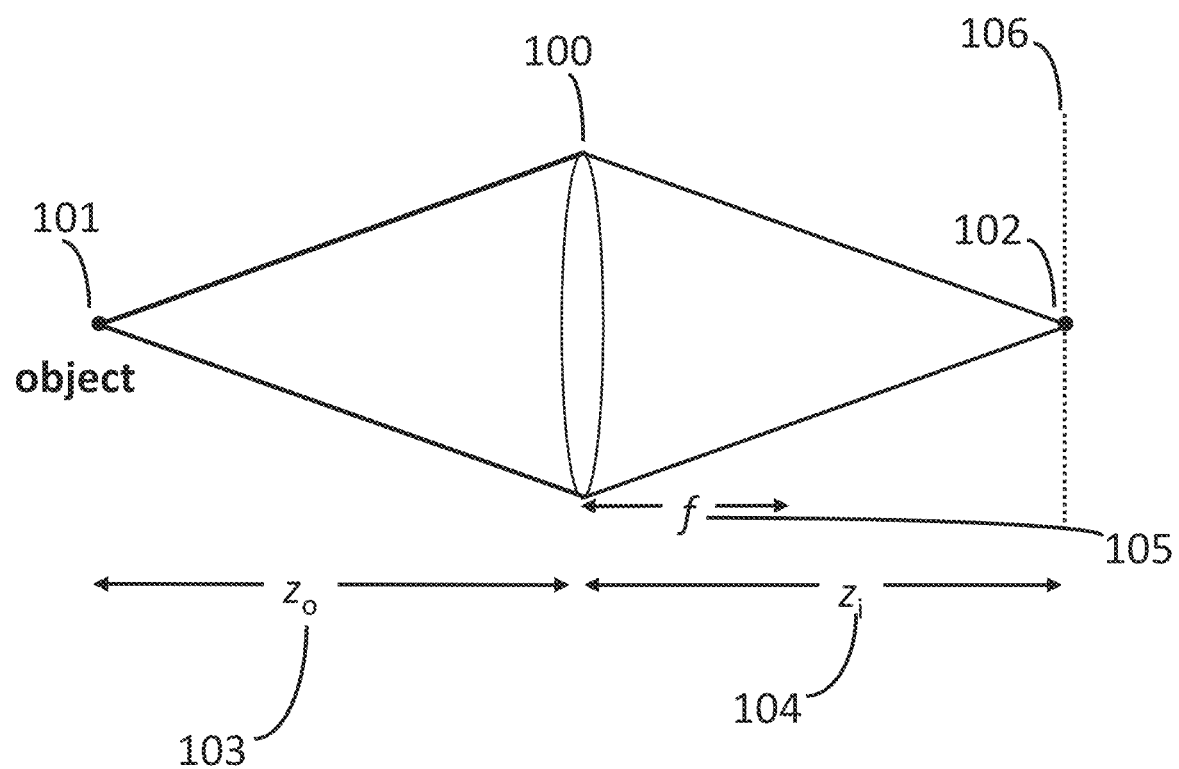
FIG. 1. A diagram depicting a conventional imaging lens wherein the received electromagnetic (EM) radiation from the object is focused to only one plane of focus.

In classical optical imaging, a beam of light is emitted or reflected from an object, and is then collected by a lens. In the simplest case, the light beam is focused by this lens to create an image at a focal plane. The image is two-dimensional as shown in FIG. 1 depicting a lens 100 with focal length 105 off creating at a focal plane 106 an image 102 of an object 101, and it is not possible to discern three-dimensional (3D) information about the object 101 above or below the plane of focus. Any information above or below the plane of the object is not translated to the plane of focus of the lens and is lost.

While other lenses can be added to the system to improve the image quality or change the magnification, the 3D information is still lost. Holographic methods enable the imaging of the 3D information in a scene. A number of holographic techniques exist in which a sample is illuminated by a laser such that interference of light reflected or emitted from a sample in combination with a reference beam creates holograms which fully describe the 3D properties of an object [Nature 161, 777-778 (1948)]. In classical holography a coherent source is split into a sample and reference beam, which then interfere with one another to create a hologram. These classical techniques, however, cannot be used to generate holograms from incoherent light. While these classical techniques cannot be used to measure incoherent light emissions, such as from a fluorescent sample, scanning holography has been proposed in which an interference pattern is scanned across a sample to excite fluorescence and then correlated with a sample beam to create a hologram [Opt. Lett. 22, 1506-1508 (1997)]. The scanning holography technique, however, is complex, and as a multibeam process it suffers from stringent alignment requirements and is sensitive to environmental instability because of the need to prevent any vibration in the system.

Figure 2:
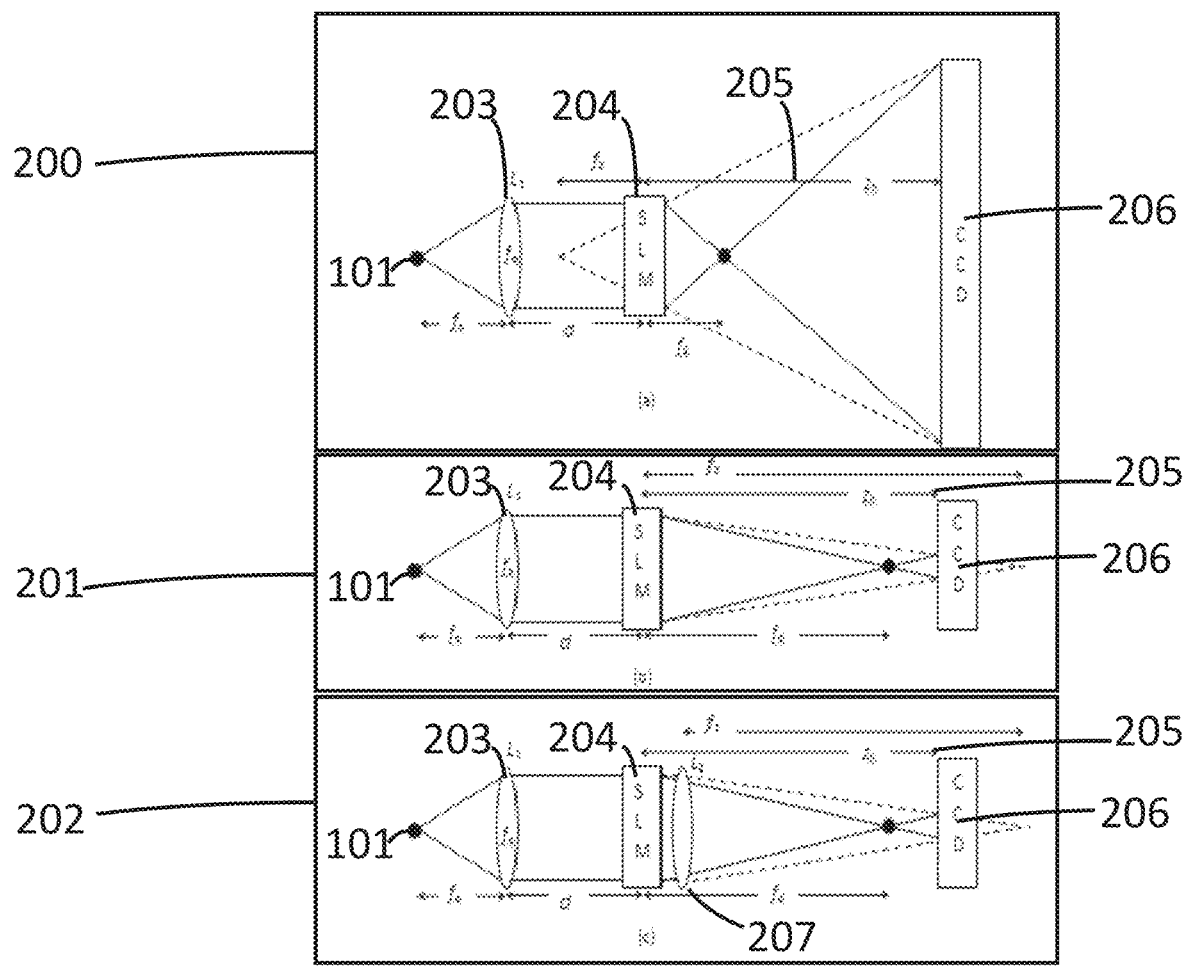
FIG. 2. A diagram depicting three configurations for Fresnel Incoherent Correlation Holography (FINCH) imaging using a spatial light modulator (SLM) to produce the reference and sample beams.

Another technique for incoherent holography invented by one of the present inventors in 2006 [U.S. Pat. No. 8,542, 421; Opt. Lett. 32, 912-914 (2007)] is dubbed FINCH for Fresnel Incoherent Correlation Holography. FINCH creates holograms from an object emitting incoherent light in a single beam system by self-interference from two spherical waves originating from the object. Three example configurations of FINCH using a spatial light modulator (SLM) are shown in FIG. 2 [adapted from Opt. Exp. 19, 26249-26268 (2011)]. Described in FIG. 2 is 200 FINCH with two diffractive lenses displayed on the SLM 204, in which one ($f_d$) is positive and the other ($f_2$) is negative. The diffractive lenses focus the light received from the object 101 through an intermediate lens 203 into a hologram recorded by a CCD camera 206 at a distance 205 ($z_h$) away from the SLM. Described in 201 is FINCH with two diffractive lenses on the SLM 204, in which both lenses are positive ($f_d$ is the shorter focal length, $f_2$ the longer). The remainder of this type of FINCH is similar to that in 200. In 202 is a practical setup that emulates the setup of 201, with one positive diffractive lens ($f_d$) displayed on the SLM 204 and one positive glass lens 207 ($f_2$) placed near to the SLM. One skilled in the art will understand that in the previous paragraph and throughout this document, the SLMs or other elements that replace the SLMs are not limited to displaying only one or two lenses, and that they may display three or more lenses or other phase patterns as desired for advantageous application to the holographic process.

FINCH has shown potential for fluorescence microscopy [J. Rosen and G. Brooker, "Non-scanning motionless fluorescence three-dimensional holographic microscopy" Nat. Photonics 2, 190-195 (2008)], and much work has been done to perfect the technique into a useful high resolution 3D imaging technique. The concept that a 3D image could be obtained from incoherent sources by a holographic process, without lasers, scanning or axial translation or the need to capture images at multiple planes of focus to create a 3D image is appealing. The field has now advanced as a result of additional work from the inventors [G. Brooker, N. Siegel, V. Wang, and J. Rosen, "Optimal resolution in Fresnel incoherent correlation holographic fluorescence microscopy," Opt. Express 19, 5047-5062 (2011); J. Rosen, N. Siegel, and G. Brooker, "Theoretical and experimental demonstration of resolution beyond the Rayleigh limit by FINCH fluorescence microscopic imaging," Opt. Express 19, 26249-26268 (2011); B. Katz, J. Rosen, R. Kelner, and G. Brooker, "Enhanced resolution and throughput of Fresnel incoherent correlation holography (FINCH) using dual diffractive lenses on a spatial light modulator (SLM)," Opt. Express 20, 9109-9121 (2012); N. Siegel, J. Rosen, and G. Brooker, "Reconstruction of objects above and below the objective focal plane with dimensional fidelity by FINCH fluorescence microscopy," Opt. Express 20, 19822-19835 (2012)] and others (P. Bouchal, J. Kapitan, R. Chmelik, and Z. Bouchal, "Point spread function and two-point resolution in Fresnel incoherent correlation holography," Opt. Express 19, 15603-15620 (2011); X. Lai, Y. Zhao, X. Lv, Z. Zhou, and S. Zeng, "Fluorescence holography with improved signal-to-noise ratio by near image plane recording," Opt. Lett. 37, 2445-2447 (2012); O. Bouchal and Z. Bouchal, "Wide-field common-path incoherent correlation microscopy with a perfect overlapping of interfering beams," J. Europ. Opt. Soc.—Rap. Pub. 8, 13011 (2013)) including the demonstration that the FINCH optical system is inherently super-resolving (J. Rosen, N. Siegel, and G. Brooker, "Theoretical and experimental demonstration of resolution beyond the Rayleigh limit by FINCH fluorescence microscopic imaging," Opt. Express 19, 26249-26268 (2011).; B. Katz, J. Rosen, R. Kelner, and G. Brooker, "Enhanced resolution and throughput of Fresnel incoherent correlation holography (FINCH) using dual diffractive lenses on a spatial light modulator (SLM)," Opt. Express 20, 9109-9121 (2012); N. Siegel, J. Rosen, and G. Brooker, "Reconstruction of objects above and below the objective focal plane with dimensional fidelity by FINCH fluorescence microscopy," Opt. Express 20, 19822-19835 (2012)) Recently it has been shown that the reason for this is that FINCH overcomes the Lagrange invariant (X. Lai, S. Zeng, X. Lv, J. Yuan, and L. Fu, "Violation of the Lagrange invariant in an optical imaging system," Opt. Lett. 38, 1896-1898 (2013) [10]). More recently FINCH holograms have been created using electrically modulated transmission liquid crystal optics (G. Brooker, N. Siegel, J. Rosen, N. Hashimoto, Makato Kurihara and A. Tanabe, "In-line FINCH super resolution digital holographic fluorescence microscopy using a high efficiency transmission liquid crystal GRIN lens," Opt. Lett. 38(24), 5264-5267 (2013). Additionally, the inclusion of a Nipkow disk has been used to create confocal FINCH images, (N. Siegel and G. Brooker, "Improved axial resolution of FINCH fluorescence microscopy when combined with spinning disk confocal microscopy," Optics Express Vol. 22, pp 22298-22307 (2014) and U.S. patent application 62/023, 958). The FINCH holographic process is the subject of several patents including U.S. Pat. No. 8,009,340 issued on Aug. 30, 2011; U.S. Pat. No. 8,179,578 issued on May 15, 2012; U.S. Pat. No. 8,405,890 issued on Mar. 26, 2013; U.S. Pat. No. 8,542,421 issued on Sep. 24, 2014; and Japanese patent JP 5611588 issued on Sep. 12, 2014.

While FINCH is a considerable advance in incoherent holography, the SLM method of creating the two interfering beams still requires two different lenses and those lenses require perfect alignment. Example embodiments of the invention disclosed in this application create optically more perfect beams than any of the prior techniques for incoherent holography. Beams modulated by example embodiments do not suffer from quantization error that is inherent in using quantized devices such as pixelated liquid crystal SLMs or Fresnel lenses or GRIN lenses with discrete phase shifting regions and sharp boundaries between the properties of neighboring regions. These errors include loss of light into undesired diffraction orders, stepped instead of smooth phase profiles of the modulated beams, incomplete phase modulation, significant chromatic shift in focal lengths, and defects in the phase profiles of the modulated beams due to the mechanical structure of SLMs, GRIN lenses, etc. Beams modulated by some example embodiments may avoid all these defects, since these embodiments may not contain discrete regions with sharp boundaries (i.e. it is not quantized). There is no diffraction off of mechanical frameworks and thus no loss to undesired diffraction orders; and there is smooth continuous modulation of the phases of the modulated light; and there is only standard refractive chromatic dispersion error, which can be better corrected than the diffraction-induced chromatic dispersion. The SLM method used involves displaying one or more different lens patterns on a spatial light modulator (SLM) [Opt. Lett. 32, 912 (2007); Opt. Exp. 19, 5047 (2011)] but may be prone to low hologram quality due to lens sampling and to low efficiency due to higher-order diffracted images. These issues may lead to poor interference, high background and low resolution due to the limited number of pixels and bit depth of the SLM. Furthermore, since SLM's are reflective, the optical arrangement requires that the SLM be positioned on an angle from the optical axis of the imaging system or arranged on a beam splitter to circumvent mounting it on an angle. However, angled incidence of the original light beam makes calibration of the SLM difficult for multiple focal lengths, and use of a beam splitter significantly reduces the light budget of the optical system [Opt. Exp. 19, 5047 (2011)].

Figure 3:
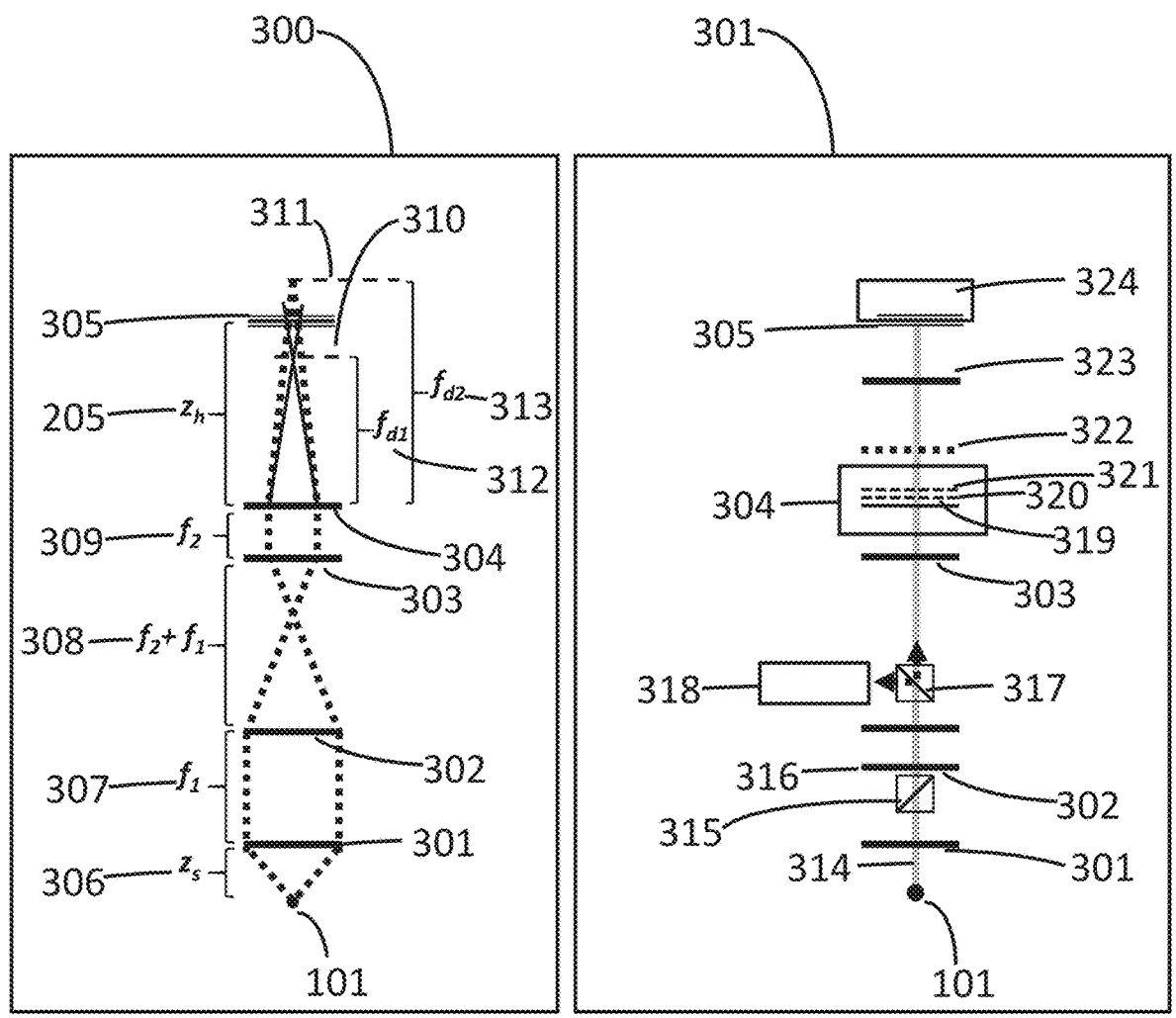
FIG. 3. Schematic of a FINCH fluorescence microscope using Thin Liquid Crystal Gradient Refractive Index (TL-CGRIN) lens.

FIG. 3 shows a detailed schematic of a more recent method, which has been to use a glass lens in conjunction with a liquid crystal Fresnel lens or Gradient Refractive Index (GRIN or TLCGRIN) lens in a totally transmissive arrangement, reported in Opt. Lett. 38, 5264-5267 (2013). On the left side of the FIG. 300 is depicted the detailed ray diagram for a FINCH hologram of a point. The light leaves the object 101, traveling a distance 306 to be collected by the objective lens 301. The collimated light leaving 301 propagates the distance 307 to the first of two relay lenses, 302. The light travels the distance 308 to the second relay lens 303 and then a further distance 309 to the GRIN assembly 304. The GRIN assembly 304 with two effective focal lengths 312 and 313 creates the two waves that propagate to the distances 310 and 311, while the hologram 305 is located at the plane removed from the GRIN assembly 304 by the hologram distance 205. On the right side of the FIG. 301 is depicted the detailed arrangement of the components in the referenced microscope system. All optics are centered on the optical propagation axis 314. The dichroic beamsplitter and emission filter 315 and 316 are necessary for fluorescence microscopy in order to introduce the excitation light into the sample, and to separate the emission light that is received form any stray reflected excitation or other light, while the polarizing beamsplitting cube 317 is used to polarize the received light at an angle of 45 degrees to the active axis of the GRIN assembly. The rejected polarization component from this polarizer is sent to the camera 318 that records a standard image. The GRIN assembly 304 contains a glass lens 319, and active GRIN 320 and an inactive GRIN 321. The glass lens focuses all the light passing through it, while the active GRIN adds additional focal length to the light that passes parallel to its axis, and the inactive GRIN serves to compensate for side effects of the light passing the active GRIN. Thus the two focal lengths 312 and 313 are created. Distances are corrected to account for the optical path through the glass of the BS cubes. The final two optics are the phase shifting waveplate 322 and the output polarizer 323, which modulate the overall phase of the hologram and increase interference efficiency, respectively. The hologram plane 305 is between the two focal lengths 312 and 313, and a camera 324 is used to record the hologram. FIG. 3 is adapted from Optics Letters 38, 5264-5267 (2013].

While the TLCGRIN method is an improvement over the SLM, it still is limited by the reduced imaging quality of a Fresnel lens or the limited number of graded regions used to create a liquid crystal GRIN lens. Furthermore it is challenging to make GRIN lenses with sufficient aperture and shortness of focal length for high quality imaging and compactness of a holographic system. In this GRIN lens system example, the GRIN lens had a 5000 mm focal length and the glass lens a 300 mm focal length. Furthermore both the SLM and GRIN lens systems require electrical control of the devices in addition to compensating lenses to control for dispersion in the liquid crystal material. The TLCGRIN method requires external power to induce the birefringent effect of differential modulation of different polarization components of the received light. Since the GRIN lens has multiple rings concentrically arranged around its center, each of which has a discrete constant phase shift value with relatively sharp boundaries between rings, it is quantized, though it is not as severely quantized as an SLM. This combination of focal lengths creates a spacing factor between the two focal lengths of less than 3%, which reduces the axial depth of 3D objects that can be reliably imaged by the holographic system [Opt. Exp. 20, 9109 (2012)].

Figure 4:
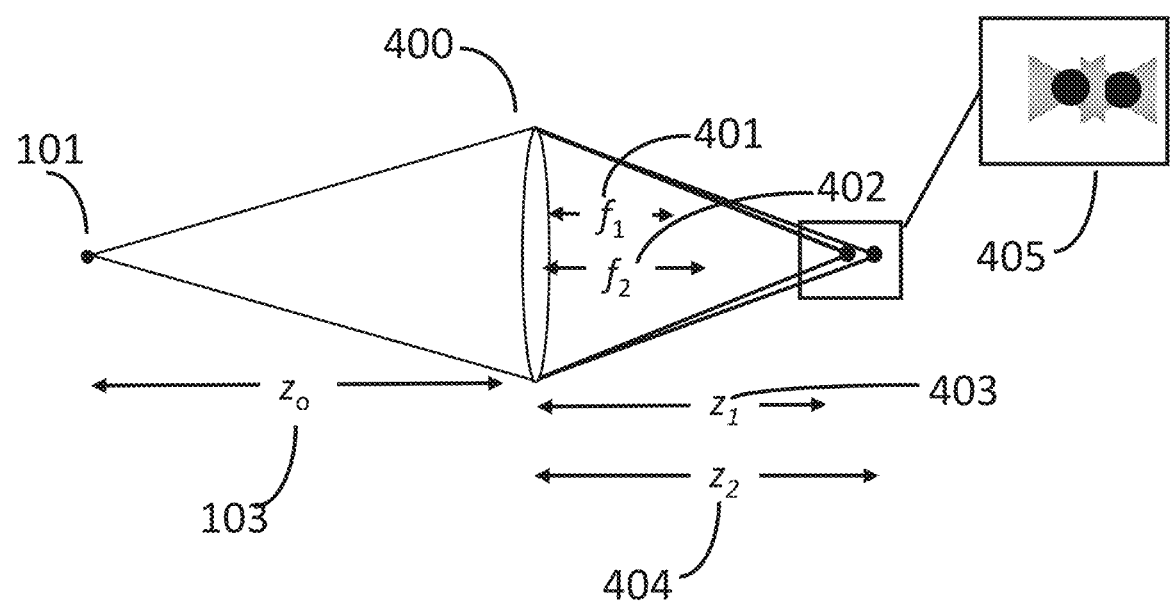
FIG. 4. A birefringent lens with two focal lengths $f_1$ and $f_2$, according to one or more example embodiments.

To address this, the inventors have discovered a unique use for spherical lenses that can be constructed of birefringent materials. FIG. 4 shows an example of a lens 400 made from a birefringent material, according to some embodiments. Birefringent substances have two distinct polarization sensitive refractive indices and thus lenses made from such materials always have two focal lengths $f_1$ 401 and $f_2$ 402 and produce blurry images when randomly polarized light is passed through them, since a single sharp plane of focus is not possible unless the image is viewed through a polarizer. When randomly polarized light is passed through the lenses, a single sharp focus cannot be obtained since the multiple refractive indices of the material cause the lens to display a different focus for light of p or s polarization, creating two images at distances 403 and 404. Thus these lenses yield a doubled or blurry image 405, which is generally undesirable in standard optical applications. For this reason birefringent materials are not typically used to make optical lenses because of this ordinarily undesirable property; evidence of this is that birefringent lenses are not readily commercially available from optical supply houses. Currently birefringent lenses must be custom made and there are few reports in the literature of their construction [Proc. of SPIE Vol. 6018, 601812 (2005); Meas. Sci. Technol., 17, 1367 (2006); Optik 118, 335-339 (2007)]. However since birefringent materials such as calcite, barium borate, lithium niobate and quartz can be readily worked just like glass, it is possible to readily prepare lenses of birefringent materials to any lens specification, given a rationale for making them.

The inventors have discovered that the simultaneous usage of the multiple focal lengths of birefringent lenses can be very advantageous to create very high quality holograms that can reveal the three dimensional information of objects. Embodiments of the invention can be applied to many forms of holography including FINCH and operates in an electrically independent manner with optical characteristics that yield unmatched holographic image quality which exceeds the performance of standard imaging methods. Furthermore, in addition to holographic imaging applications, the embodiments also enhance and simplify other forms and uses of holography and interferometry. For an example, birefringent lenses were already found in nature long ago in the eye of the trilobrite, a creature that lived in the sea 450 million years ago. These eye lenses were called schizochroal and made of birefringent calcite. One might speculate that lenses made of calcite became extinct during evolution because of their undesirable optical properties. Calcite is an optically clear material with two different refractive indices depending upon the plane of polarization. Even though it is not a good material to make standard lenses, its polarizing properties are exploited to make polarizers and polarization sensitive devices such as Glan-Taylor prisms. Calcite is used because it is optically clear and its crystal structure can efficiently pass a single axis of linear polarization. However if lenses are made of calcite, because of the different refractive indices at the two planes of polarization, two distinct polarization sensitive focal lengths of those lenses are observed (see https://community.dur.ac.uk/g.d.love/downloadable/china05.pdf). However with mixed polarization light, which is the common form of light in the environment, a blurred image would result if lenses were made of birefringent materials. While the trilobrite had calcite for its lens material, one might wonder if its vision was blurred or if it could see the two focal planes because its photoreceptors were cross polarized.

However, an imaging method that required different aligned copies of the same image could benefit greatly from just such a birefringent lens. Incoherent holography, a class of holography that includes FINCH and other methods [Opt. Lett. 32, 912 (2007); Nat. Photonics 2, 190 (2008); Opt. Express 19, 5047 (2011); Opt. Express 19, 26249 (2011); Opt. Express 20, 19822 (2012); Opt. Lett. 38, 3922 (2013); Opt. Lett. 38, 5264-5267 (2013), and U.S. Pat. Nos. 8,009, 340, 8,179,578 and 8,542,421], is a technique for creating holograms from the interference of two copies of the same image, or from any single EM radiation wave that is split into two copies, and has been demonstrated using polarization-sensitive optical elements (PSOEs) such as SLMs and liquid crystal Fresnel and GRIN lenses. These PSOEs, which are not classical refractive spherical lenses but which may be diffractive or refractive in operation, serve to split the image beam into two parts with differing spherical curvatures. In the further description of the process in relation to embodiments, the inventors consider light emanating (by emission or reflection or any other process) from a single infinitesimally small object point, which creates a "point hologram" that suffices to describe the system; extended objects larger than this create holograms that are simply the sums of the holograms of all the differing points constituting the extended object. A broad, collimated laser beam may be used as a model source of EM radiation in these systems, since the image of such a beam is a diffraction-limited spot as from an infinitesimal point source. This aspect enables the empirical characterization of the best response of any such system.

Figure 5:
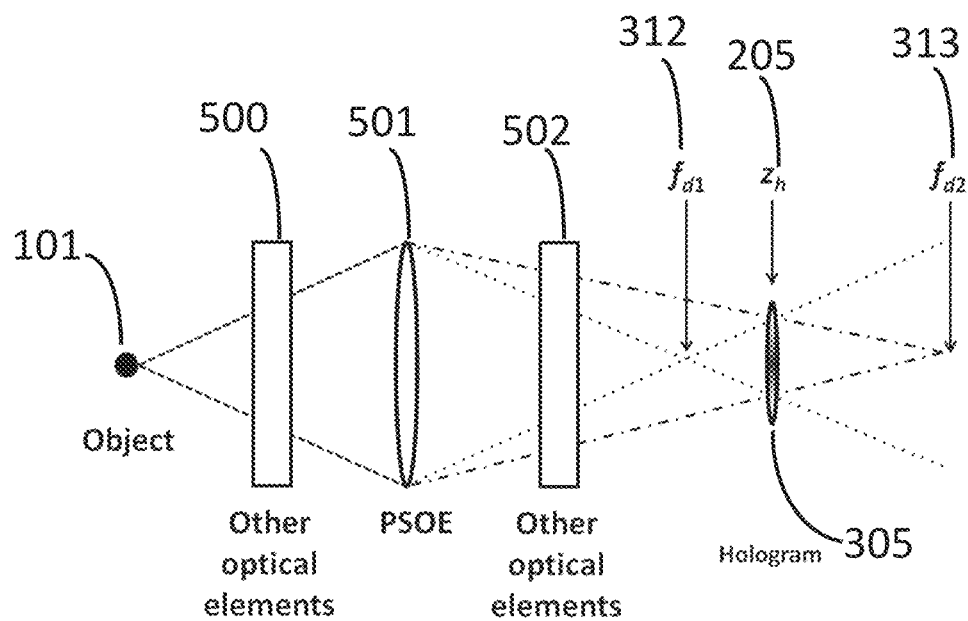
FIG. 5. A generalized scheme for creating a FINCH hologram according to one or more example embodiments.

FIG. 5 shows a schematic of the FINCH process highlighting the role of the PSOE. The PSOE 501 has two different focal lengths, of which $f_{d1}$ is the shorter and $f_{d2}$ is the longer. Other optical elements or groups 500, 502 may be used to make specific alterations in the overall phase, polarization, aberration correction or magnification or hologram size of the system, but the beam separation is solely a result of the use of the PSOE. After emanating from the object and possibly passing other optical elements, the light wave is split into two waves, of differing focal lengths by the PSOE. This splitting can be accomplished by reflecting off of or transmission (e.g, by refraction or diffraction) through the PSOE. These waves propagate through the same space in the same direction, and are termed the signal and reference or $f_{d1}$ and $f_{d2}$ waves. Currently this is accomplished in one of two ways:

1. By polarization: the received wave hitting the PSOE is polarized at 45 degrees to the polarization axis of the PSOE. Thus half of the wave with polarization component projected parallel to the PSOE polarization axis is given the curvature encoded in the PSOE, while the half of the wave with polarization component projected perpendicular to the PSOE polarization axis maintains its original curvature. The result is the $f_{d1}$ and $f_{d2}$ waves.
2. By sampling of the PSOE: The PSOE is divided into more than one portion, each of which is encoded with differing spherical phases. The portions may be interspersed with each other and not contiguous. The received wave hitting the PSOE is polarized entirely parallel to the PSOE polarization axis, and the wave emerging from the PSOE has different portions with differing curvatures added corresponding to the curvatures encoded in the different portions of the PSOE. If the PSOE has two portions, the two wave portions emerging from the PSOE are termed $f_{d1}$ and $f_{d2}$. However the PSOE can have more than two portions, in which case there are light waves termed $f_{d3}$, etc.

Current technologies serving as polarization-sensitive PSOEs to generate the $f_{d1}$ and $f_{d2}$ waves include digital spatial light modulators (SLMs), liquid crystal (LC) Fresnel lenses and LC gradient refractive index (GRIN) lenses. In some configurations these components are also used in conjunction with classical lenses, or more than one of the components may be used in conjunction with each other.

After propagating from the PSOEs, the two waves interfere and create the hologram recorded at the detector ($z_h$) plane. The detector may be a CCD, CMOS or other camera or image capture device as well as a point detector or solid-state device such as an avalanche photodiode. Optionally the waves may pass through a variable phase shifter and a polarizer. To reconstruct a point or image and provide the basis to remove bias and the twin image in holography, the detector captures two or more raw holograms, in which the phase of one of the beams is set to differ by a predetermined amount in subsequent raw holograms, to allow for the recovery of the complex hologram that fully captures the phase characteristics of the original EM source [Optics Letters 22(16), 1269-1270 (1997)]. The collection of raw holograms with such different phase factors is critical to achieving the optimal result with FINCH and similar holography methods.

One of the key parameters in this process is the relationship between the focal lengths $f_{d1}$ and $f_{d2}$ and the hologram recording plane at $z_h$. Holograms may be recorded at any point after the PSOE, but the optimal hologram quality is made possible when the two waves obey a condition of maximal spatial overlap. The condition to ensure maximum overlap between the $f_{d1}$ and $f_{d2}$ beams is met when the hologram is recorded at the plane $$z_h = 2\frac{f_{d1}f_{d2}}{(f_{d1}+f_{d2})}. \qquad (1)$$

This relationship may also be expressed as $$z_h = (1+s)'f_{d1} = (1-s)'f_{d2}, \qquad (2)$$

where the spacing factor s obeys the equality:

$$s = \left|\frac{f_{d2}-f_{d1}}{f_{d2}+f_{d1}}\right|. \qquad (3)$$

As s increases (the distance between $f_{d1}$ and $f_{d2}$ increases), the point hologram at the optimal $z_h$ plane also increases in size, as described by the following equation:

$$R_H = s'R_0, \qquad (4)$$

where $R_H$ is the aperture radius of the hologram and $R_0$ is the aperture radius of the wave at the PSOE or equivalent. This size increase renders the point hologram more easily resolvable by recording devices but decreases the peak intensity of the hologram. There are other factors [Opt. Express 20, 9109 (2012)] that also establish upper and lower bounds for s. It is very desirable to have complete control over s over a wide range in order to be able to optimize the holographic system for all possible variables such as magnification of the image, spatial size of the point hologram, fringe spacing and number of fringes therein, and intensity of the light at the hologram plane. The s factor may not itself change the resolution of the image coded by the hologram, but does affect the ease with which the hologram may be recorded; and further, any arrangement used to change s may affect other image factors such as magnification and depth of field. In some aspects, the capability provided in certain example embodiments to vary the s factor, yields the benefit of the configurability available in the SLM-based holography techniques while yielding higher quality interference patterns than any GRIN-based holography techniques.

Each of the three current technologies mentioned above can serve to create $f_{d1}$ and $f_{d2}$ by reflection off of or transmission through the PSOE, but each also bears significant disadvantages:

1. SLMs are easily adjustable to produce different focal length PSOEs at will, in the form of digitized Fresnel phase patterns, but suffer from low focusing efficiency to the desired image, as diffraction from the pixilated digital SLM causes significant light loss into transverse foci of higher diffraction orders. Additionally, the PSOEs created on SLMs suffer from significant variability in focal length as a function of light wavelength (an effect termed chromatic aberration) which may degrade performance in hologram formation.
2. LC Fresnel lenses are polarization sensitive and do not suffer from higher-order transverse foci, but may display other axial foci and certainly suffer from significant chromatic aberration. They are also not adjustable, and offer only a single nominal focal length.
3. LC GRIN lenses have focal lengths adjustable as a function of applied voltage, and less chromatic aberration than SLMs or LC Fresnel lenses, but have very long focal lengths that require them to be paired with regular refractive lenses in order to achieve reasonable overall focal lengths. Even when combined with refractive lenses, LC GRIN lenses offer limited possibilities for spacing factor. Finally, currently used LC GRIN lenses are quantized approximations of lenses (because of the practical limitation of the number of differentially refractive zones possible) and thus impose spatial distributions of light in the unfocused beams that can cause reduced interference efficiency and accuracy of focal length calculation.

Figure 6:
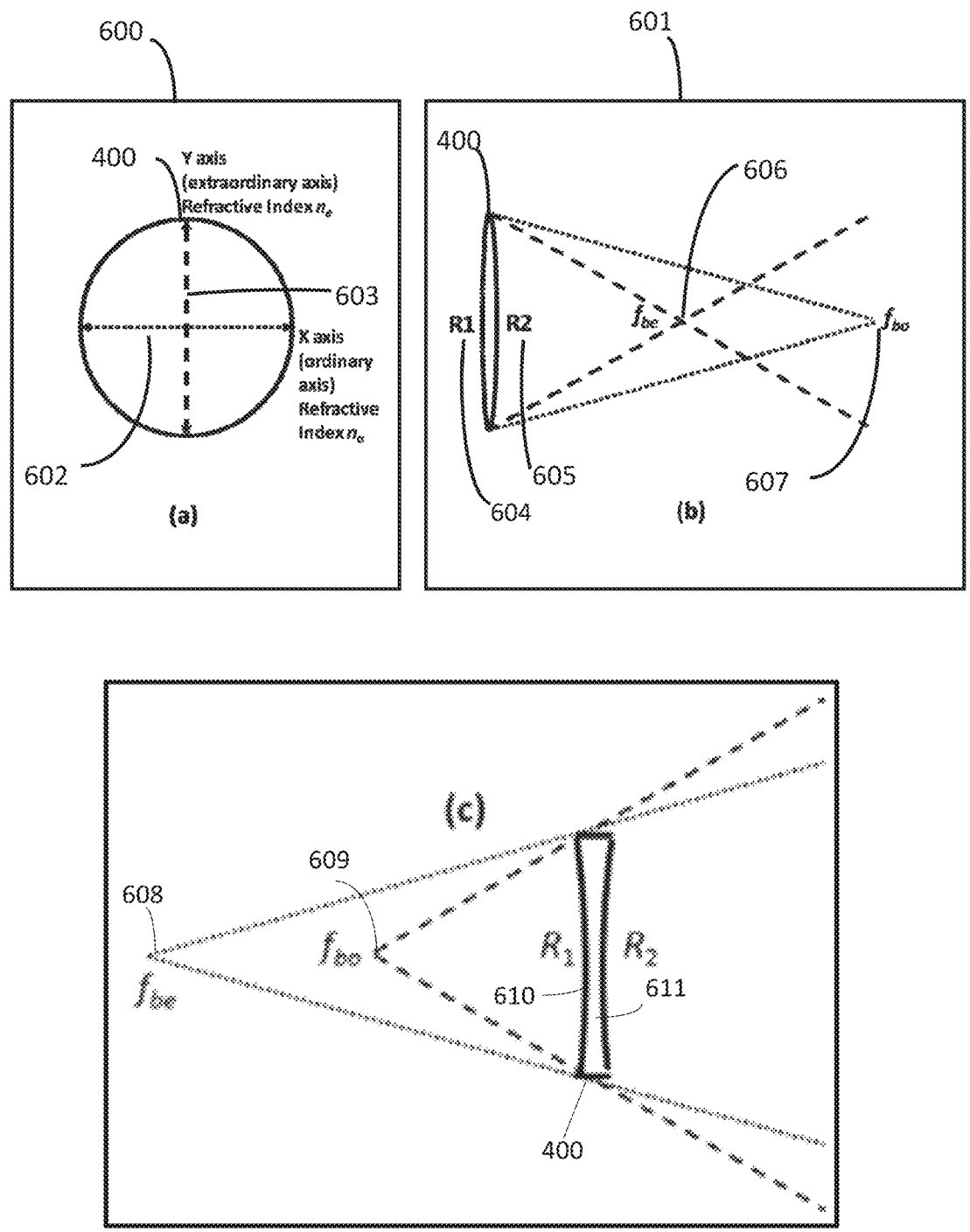
FIG. 6. The differing focal lengths of a birefringent lens resulting from the differing refractive indices in the transverse plane of the lens, according to one or more example embodiments.

There is a pressing need in this field for the introduction of a device to create the $f_{d1}$ and $f_{d2}$ beams with equivalent quality to that of a spherical refractive lens and without the disadvantages mentioned above, and with increased flexibility in the spacing factor s. Birefringent materials possess two or more refractive indices along different propagation directions in the material, termed the ordinary and extraordinary axes. These axes have refractive indices denoted $n_o$ and $n_e$, respectively. Since the focal length of a lens is dependent in part on the refractive index of the material comprising the lens, these materials can be used to create spherical lenses that possess two different polarization-dependent focal lengths, each of which produces a spherical beam and a focal spot of equal quality to those of a standard glass lens. FIG. 6 shows a schematic of a birefringent lens (BRL) focusing light of differing polarization to different focal planes. FIG. 6a 600 shows a cross-section of a BRL, with the ordinary 602 and extraordinary 603 refractive indices projected along the x and y Cartesian axes of the lens. FIG. 6b 601 shows the focal lengths $f_{be}$ 606 and $f_{bo}$ 607 of the single birefringent lens (with radii of curvature $R_1$ 604 and $R_2$ 605 for the two surfaces of the lens) for light polarized parallel to the extraordinary axis and for light polarized parallel to the ordinary axis of the lens, respectively. FIG. 6b shows a convergent lens 400. FIG. 6c shows the focal lengths $f_{be}$ 608 and $f_{bo}$ 609 of the single birefringent divergent lens 613 (with radii of curvature $R_1$ 610 and $R_2$ 612 for the two surfaces of the lens). The quality of the beams and the focal spots of the BRL is much improved over those from diffractive PSOEs mentioned above. A perfect FINCH point hologram is composed of many well-modulated spherical fringes following the sinusoidal Fresnel zone plate, in which the fringes are all perfectly spherical, concentric with fringe size that decreases in proportion to distance from the center, and in which the dark fringes do not contain any light at all; the maximum quality FINCH hologram of a real object is obtained as the sum of many point holograms originating from the different points of the object. To obtain a perfect or nearly perfect FINCH hologram it may be necessary that a reference and sample beam path interfere such that the image size is identical or nearly identical for both beams at a hologram plane. This can be readily accomplished by adjusting the focal lengths and shape of the birefringent lenses. In FIG. 6 a schematic is shown where the beams intersect at a plane between the focal lengths of the birefringent lens. Birefringent Refractive Lenses used in example embodiments, such as those shown in FIG. 6, offer advantages over PSOEs in several aspects of incoherent hologram generation, including:

1. Elimination of the noise and image artifacts due to unwanted diffraction orders of PSOEs or the quantization error inherent in digital or binary representations of lenses.
2. The possibility of correction of chromatic, spherical and other aberrations by use of corrective optics including non-birefringent and birefringent optics.
3. Precise and flexible tailoring of the spacing factors by choice of BRL material, curvature and associated optics.
4. Simplification of and size reduction of the optical assembly by removal of electronic and reflective components.

Some example embodiments of the invention covers, at least in part, the use of a BRL, alone or in conjunction with other refractive lenses or other optical elements, to effect the splitting of the received wave into two orthogonally polarized waves with differing spherical curvature to create holograms. Birefringent crystals have differing refractive indices along their ordinary and extraordinary crystal axes, and by cutting (and/or grinding and polishing) a lens from such a material in the proper orientation with these two axes perpendicular to each other and both lying in the plane of the lens orthogonal to the direction of light propagation through the lens, a refractive lens with special properties may be created. These special properties are that the lens focuses light polarized parallel to one of its polarization axes (for example, the ordinary axis, also identified here as the x axis in a Cartesian system) to a given focal plane, while the light polarized parallel to the other axis (the extraordinary or y-axis) is focused to a different focal plane (see FIG. 6). This may be easily understood by referring to the thin lens equation:

$$\frac{1}{f} = (n-1)\left(\frac{1}{R_1} - \frac{1}{R_2}\right), \text{ or } f = \frac{1}{(n-1)}\left(\frac{R_1 R_2}{R_2 - R_1}\right) = \frac{R_{\text{eff}}}{(n-1)}, \quad (5a)$$

$$\frac{1}{f} = (n-1)\left(\frac{1}{R}\right), \text{ or } f = \frac{R}{(n-1)} = \frac{R_{\text{eff}}}{(n-1)}, \quad (5b)$$

$$R_{\text{eff}} = \begin{cases} \frac{R_1 R_2}{R_2 - R_1}, & \text{for a lens with two curved sides} \\ R, & \text{for a lens with one curved side} \end{cases} \quad (5c)$$

with f being the focal length of the lens, n the refractive index of the lens material, $R_1$ and $R_2$ the radii of curvature of the two sides of the lens, and $R_{\text{eff}}$ is the "effective" total curvature of the lens. Equation 5b is for the specific case of a lens with one flat side (plano-concave or plano-convex)

and one curved side with curvature R. As called out in equation 5c, $R_{eff}$ for a lens with two curved sides is exactly equivalent to R of a plano-concave or plano convex lens. Equivalently to using a solid birefringent crystal, a birefringent liquid crystal material may be used to create a BRL when aligned and placed between two substrates with curvatures $R_1$ and $R_2$. Thus a single BRL, made from birefringent material with $n_o$ and $n_e$ for the ordinary and extraordinary refractive indices, has focal length $f_{bo}$ for light polarized along its ordinary axis and focal length $f_{be}$ for light polarized along its extraordinary axis. By virtue of the extraordinary axis of the lens being orthogonal to the direction of light propagation, the extraordinary axis will not impart a transverse offset to the beam as can happen in other axis orientations. The two focal lengths of the BRL may be used as the two focal lengths necessary for the holographic process, i.e. $f_{be}$ and $f_{bo}$ may be substituted for $f_{d1}$ and $f_{d2}$ in equation 3. By reference to equation 3, then, any single lens made of a given type of birefringent material will have a constant spacing factor no matter the physical curvatures of the lens:

$$s = \left| \frac{f_{be} - f_{bo}}{f_{be} + f_{bo}} \right| = \left| \frac{n_o - n_e}{n_o + n_e - 2} \right|. \quad (6a)$$

Equation (1) may be simplified as follows for a birefringent lens:

$$z_h = 2\frac{f_{be} f_{bo}}{f_{be} + f_{bo}} = \frac{2R_1 R_2}{(R_2 - R_1)(n_o + n_e - 2)}. \quad (6b)$$

However, when used in conjunction with a non-birefringent lens, each of the focal lengths of the birefringent lens combines with the single focal length $f_r$ of the non-birefringent lens to result in two new combined focal lengths, one for each polarization axis of the birefringent lens. Under the thin-lens approximation and assuming no distance between the birefringent lens and the standard lens, the focal lengths $f_{be}^\phi$ and $f_{bo}^\phi$ of the combined system are now:

$$f_{be}^\phi = \frac{f_{be}' f_r}{f_{be} + f_r}, \text{ and } f_{bo}^\phi = \frac{f_{bo}' f_r}{f_{bo} + f_r}, \quad (7)$$

and the combined spacing factor $s\phi$ of the hologram system can be increased and decreased from this constant value according to the following equation:

$$s\phi = \left| \frac{f_{be}^\phi - f_{bo}^\phi}{f_{be}^\phi + f_{bo}^\phi} \right| = \left| \frac{f_{be} - f_{bo}}{f_{be} + f_{bo} + \frac{2 f_{be} f_{bo}}{f_r}} \right|, \quad (8a)$$

and correspondingly from Equation (1)

$$z_h^\phi = 2 \frac{f_{be}^\phi f_{bo}^\phi}{f_{be}^\phi + f_{bo}^\phi} = \frac{2 R_1 R_2}{(R_2 - R_1)(n_o + n_e - 2) + \frac{2 R_1 R_2}{f_r}}. \quad (8b)$$

Note the similarity of the right-most part of equation 8a to the internal part of equation 6a, showing the additional factor for adjustment of the spacing factor. Table 1 contains the refractive indices, curvatures, focal lengths and inherent spacing factors of spherical lenses that could be made from several select birefringent material, calculated from equations 4-6, as well as corresponding altered focal lengths and altered spacing factors for systems incorporating these lenses and select glass lenses, calculated from equations 7 and 8. The collected data demonstrate the possibility to exercise total control of the spacing factor and other holography properties of BRL based systems. Some example embodiments allow the spacing factor to be freely altered between 0.001-0.33, for example, while maintaining perfect beam overlap, for the purposes of adjusting the intensity of and number of fringes in the point hologram.

TABLE 1

Refractive indices, curvatures, focal lengths and incoherent hologram parameters of selected birefringent materials.

| Birefring material | $n_o$ | $n_e$ | $R_1$ (mm) | $R_2$ (mm) | $f_{bo}$ (mm) | $f_{be}$ (mm) | S | $z_h$ (mm) | $f_r$ (mm) | $f_{bo}'$ (mm) | $f_{be}'$ (mm) | s' | $z_h'$ (mm) |
|---|---|---|---|---|---|---|---|---|---|---|---|---|---|
| Calcite | 1.66 | 1.49 | 95 | −95 | 72 | 98 | 0.150 | 83 | −166 | 128 | 237 | 0.300 | 166 |
| Calcite | 1.66 | 1.49 | 190 | −190 | 144 | 195 | 0.150 | 166 | N/A | 144 | 195 | 0.150 | 166 |
| Calcite | 1.66 | 1.49 | 380 | −380 | 289 | 391 | 0.150 | 332 | 332 | 154 | 179 | 0.075 | 166 |
| Quartz | 1.54 | 1.55 | 95 | −95 | 87 | 86 | 0.008 | 87 | −173 | 176 | 170 | 0.016 | 173 |
| Quartz | 1.54 | 1.55 | 190 | −190 | 175 | 172 | 0.008 | 173 | N/A | 175 | 172 | 0.008 | 173 |
| Quartz | 1.54 | 1.55 | 380 | −380 | 349 | 344 | 0.008 | 346 | 346 | 174 | 172 | 0.004 | 173 |
| barium borate | 1.68 | 1.55 | 95 | −95 | 70 | 86 | 0.101 | 77 | −200 | 108 | 150 | 0.164 | 126 |
| barium borate | 1.68 | 1.55 | 190 | −190 | 140 | 172 | 0.101 | 154 | N/A | 140 | 172 | 0.101 | 154 |
| barium borate | 1.68 | 1.55 | 380 | −380 | 280 | 343 | 0.101 | 309 | 100 | 74 | 77 | 0.025 | 76 |

The first column refers to the birefringent material of the lens discussed in the row.
$n_o$ and $n_e$ are the ordinary and extraordinary refractive indices of the birefringent material.
$R_1$ and $R_2$ are the radii of curvature of the birefringent lens.
$f_{bo}$ and $f_{be}$ are the ordinary and extraordinary focal lengths of the birefringent lens, as discussed in the text.
s is the inherent spacing factor of the birefringent material, as discussed in the text.
$z_h$ is the optimal hologram distance for the given combination of birefringent material and lens curvature, as discussed in the text.
$f_r$ is the focal length of an optional non-birefringent lens used in conjunction with the birefringent lens for the purpose of altering the spacing factor and optimal hologram distance.
$f_{bo}'$ and $f_{be}'$ are the altered ordinary and extraordinary focal lengths of the birefringent lens, as discussed in the text.
s' is the altered inherent spacing factor of the birefringent material, as discussed in the text.
$z_h'$ is the altered optimal hologram distance for the given combination of birefringent material and glass lens, as discussed in the text.

Figure 7:
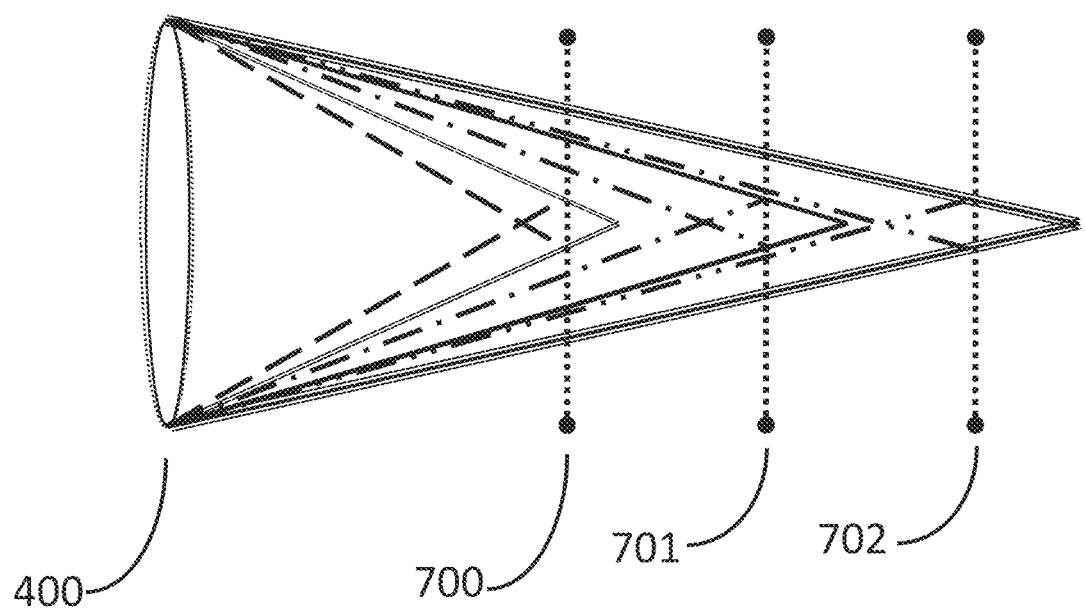
FIG. 7. Wavelength dependent shift in location of optimal hologram planes, according to one or more example embodiments.

The implications of equation 8 include that:
1. The choices of $R_1$ and $R_2$ of the birefringent lens and focal length $f_r$ of the standard lens allow any spacing factor to be achieved with a BRL made from any birefringent material. This is illustrated in Table 1, showing that for any given birefringent material, the spacing factor $s_s$ is an intrinsic property, but that the spacing factor $s¢$ of the combination of a birefringent lens and a non-birefringent lens may be adjusted up or down. The focal lengths $f_r$ of the non-birefringent lens in Table 1 were chosen to result in sets of lens combinations with the same $z_h$ but different $s¢$ (for the calcite and quartz birefringent lenses), or to show changes in both $z_h$ and $s¢$ (barium borate birefringent lens).
2. Use of a positive lens as the standard lens will reduce s' as compared to s, while use of a negative lens as the standard lens will increase s' as compared to s.
3. Hybrid lenses of any desired focal length, a chromaticity and spacing factor can be made of materials that are composed of birefringent and non-birefringent material components cemented together.
4. While compound lens compositions of birefringent materials can make a device achromatic, it should be realized that the wavelength specific refraction of each lens in a non-achromatic birefringent lens will proportionally shift the focus of each of the lens focal points made from a birefringent material. Thus the plane of maximum interference will be shifted depending on wavelength. Because of this, a feature enabled by using birefringent lenses is that wavelength specific holograms can be obtained by hologram detection at any of those wavelength specific hologram planes even though the input is polychromatic. FIG. 7 shows an example of the shift in hologram planes 700, 701, 702 as a function of variance in wavelength. Dashed lines and double lines represent a blue wavelength 700, dashed single dot lines and solid lines represent a green wavelength 701, and dashed double dot lines and triple lines represent a red wavelength 702.

One skilled in the art will understand that the above equations 5, 7 and 8 may be adjusted for use with more accurate lens equations and to account for some distance between the BRL and the glass lens.

Figure 8:
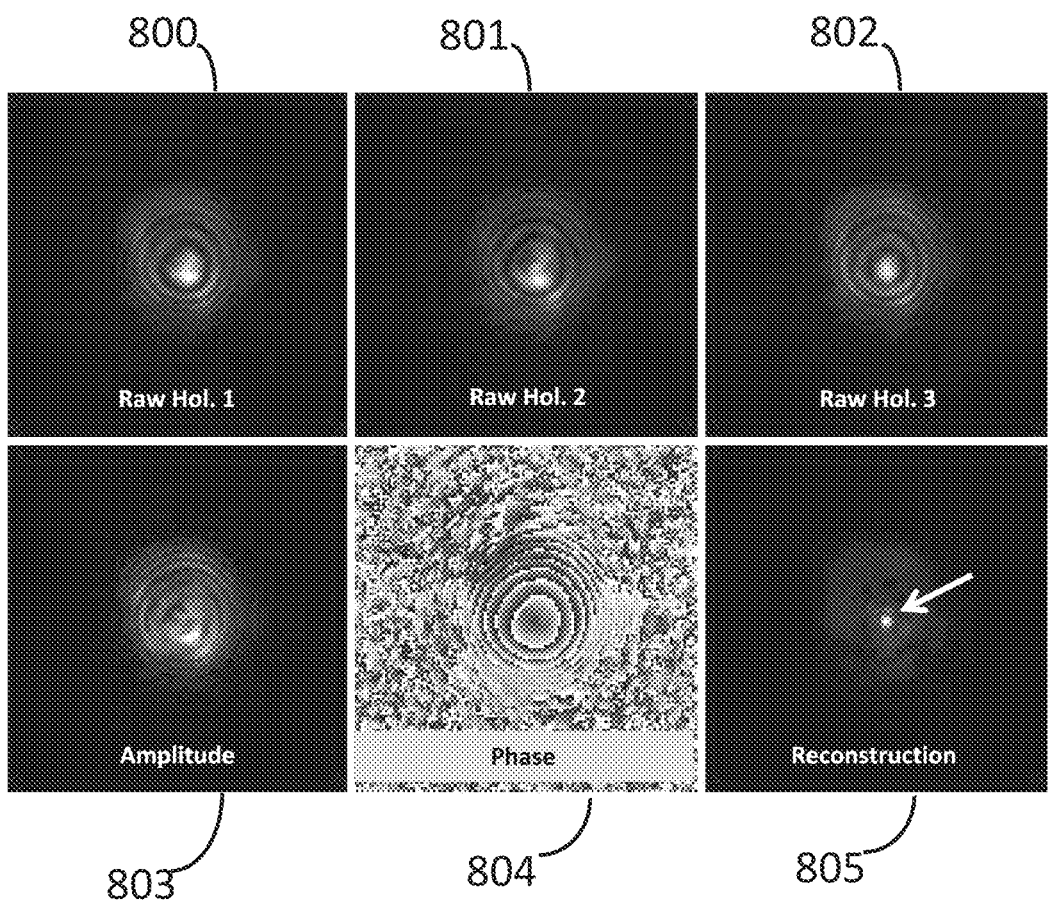
FIG. 8. Point hologram raw and processed images captured from a laser as the EM radiation source, using a FINCH system as in FIG. 3, according to one or more example embodiments.
Figure 9A:
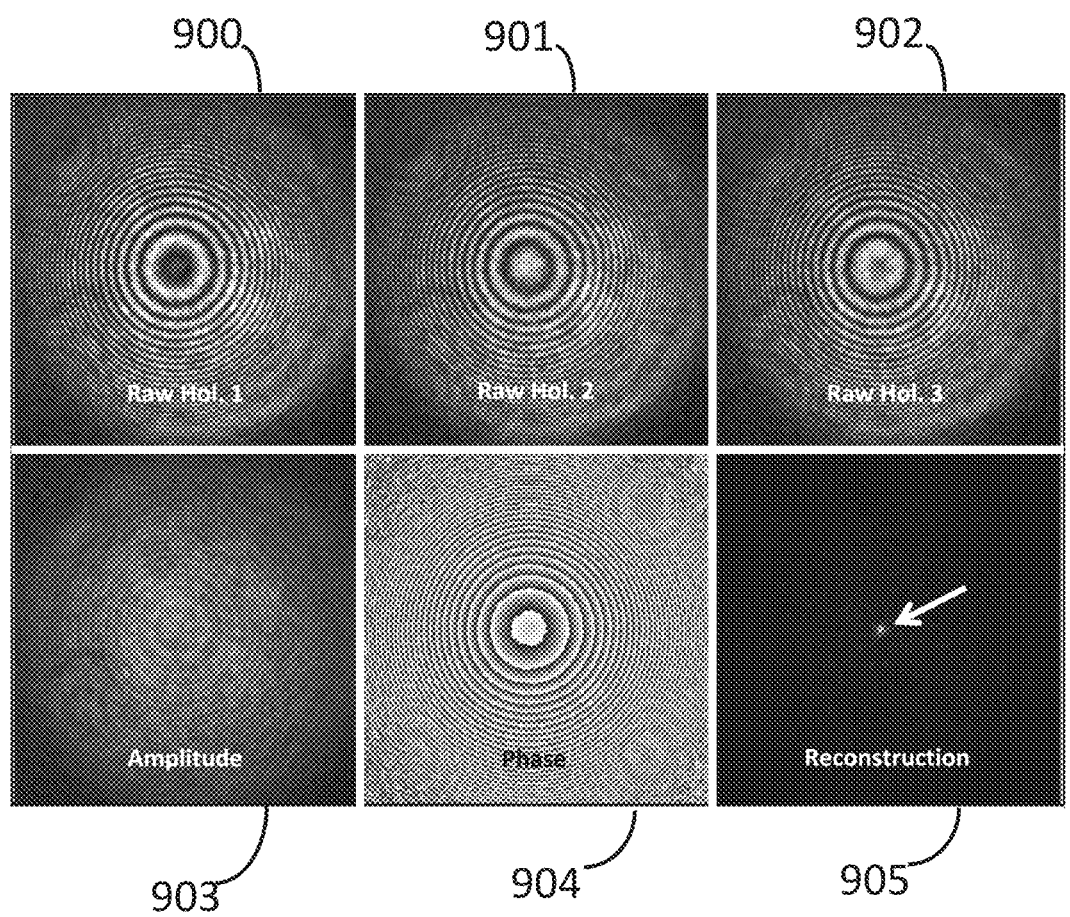
FIG. 9a. Point hologram raw and processed images captured from a laser as the EM radiation source, using a FINCH system incorporating a calcite BRL, according to one or more example embodiments.

Thus birefringent refractive lenses can be used to significantly materially improve hologram creation when used in the following configurations:
1. As the sole lens or optical element involved in hologram formation.
2. In conjunction with another paired lens or optical element to alter the spacing factor of the $f_{d1}$ and $f_{d2}$ beams, where the other lens or optical element may consist of:
   a. A single lens or optical element.
   b. A compound lens or optical element.
   c. A sequence of lenses or optical elements.
3. In conjunction with another corrective lens or optical element designed to correct spherical, chromatic or other aberrations in the birefringent refractive lens, where the corrective lens or optical element may consist of:
   a. Single, compound or multiple standard non-birefringent corrective lenses or optical elements designed to correct the aberrations of one or the other focal lengths of the birefringent refractive lens.
   b. Single, compound or multiple standard non-birefringent corrective lenses or optical elements designed to correct the average aberration of the two focal lengths of the birefringent refractive lens.
   c. Single or multiple birefringent corrective lens or optical element designed to correct the aberrations of one or the other focal lengths of the birefringent refractive lens, in which the corrective birefringent lens may be made of a different birefringent material than the hologram-forming birefringent refractive lens.
   d. Single or multiple birefringent corrective lens or optical element designed to correct the average aberration of the two focal lengths of the birefringent refractive lens, in which the corrective birefringent lens may be made of a different birefringent material than the hologram-forming birefringent refractive lens.
   e. Single or multiple birefringent corrective lens or optical element designed to correct the aberrations of one or the other focal lengths of the birefringent refractive lens, used in conjunction with standard non-birefringent lenses or optical elements, in which the corrective birefringent lens may be made of a different birefringent material than the hologram-forming birefringent refractive lens.
   f. Single or multiple birefringent corrective lens or optical element designed to correct the average aberration of the two focal lengths of the birefringent refractive lens, used in conjunction with standard non-birefringent lenses or optical elements, in which the corrective birefringent lens may be made of a different birefringent material than the hologram-forming birefringent refractive lens.
4. In conjunction with both paired and corrective lenses or optical elements of any of the kinds listed in items 2 or 3 of this list Experimental work has confirmed the improvement seen in a FINCH system when a current TLCGRIN-based system was compared with a BRL-based system. FIG. 8 shows FINCH holograms obtained using a laser as the EM radiation source, from a FINCH system configured with liquid crystal GRIN lenses and a glass lens to create two focused beams with a hologram plane between them, as in the prior art shown in FIG. 3. The top three panels 800, 801, 802 in FIG. 8 show three phase-shifted raw FINCH holograms, which are significantly distorted from the well-modulated spherical Fresnel patterns that should characterize the ideal response of a FINCH system. The bottom three panels in FIG. 8 show, from left to right, the magnitude 803 of the complex FINCH hologram, the phase 804 of the complex FINCH hologram, and finally the reconstructed image 805 of the laser beam. The magnitude shows large intensity fluctuations and both the magnitude and phase show deviations from a perfect spherical shape. The reconstructed spot shows significant background signal as well as deviations from a perfect point shape. FIG. 9 shows the results from a similar system in which the major difference was the use of a spherical calcite BRL to induce the differing phase properties between the signal and reference beams instead of a GRIN lens plus glass lens arrangement; an imaging relay lens was also used to project the hologram onto the camera after it passed the BRL. All other factors and settings, including light source, ancillary optics, polarizers, phase shifting plate and voltage, and cameras were the same as those used to produce FIG. 8. In the top row of FIG. 9a are shown three phase shifted raw holograms 900, 901, 902 as in the top three panels of FIG. 8. The raw holograms are nearly perfect representations of the desired spherical Fresnel pattern, and show many more Fresnel rings than the raw holograms in FIG. 8, a result of the much greater spacing factors possible when using a calcite BRL instead of the GRIN/glass system. In the bottom three panels of FIG. 9a, we again see, from left to right, the complex hologram magnitude 903 and phase 904 and the reconstructed image 905 of the laser. The magnitude and phase are both perfectly spherical patterns, with the magnitude free from the significant intensity fluctuations that affect the system described in FIG. 3 and used to produce FIG. 8. The phase shows a smooth slope and neat transitions at phase wrapping regions, and the reconstructed spot is point-like and free from excessive background levels. The dramatic improvement of FIG. 9a over FIG. 8 is indicative of the overall improvement in holographic imaging that BRLs can provide over other PSOEs. It should be noted that the differences in hologram diameter are caused by the fact that the s of GRIN-based FINCH is about 0.03, while that of calcite FINCH is approximately 0.11, and that this along with the secondary relay of calcite FINCH affects the size of the reconstructed spot, rendering that quantity alone insufficient for judging the performance of the birefringent lens relative to the GRIN lens. However the improvements in the raw hologram symmetry and complex hologram intensity and phase are not dependent on s and do clearly indicate the advantages of the birefringent lens in producing FINCH interference.

Figure 9B:
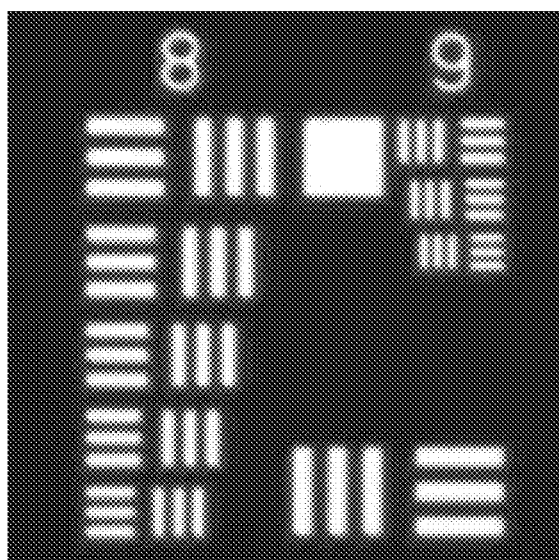
FIG. 9b. Comparative classical fluorescence microscopy and FINCH fluorescence microscopy of a standard object using a FINCH system incorporating a calcite BRL, according to one or more example embodiments, demonstrating improved image contrast and resolution in the FINCH image.
Figure 9B:
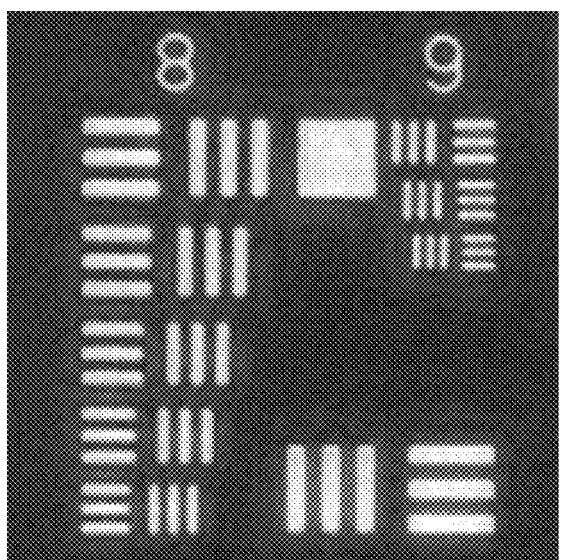
Figure 9C:
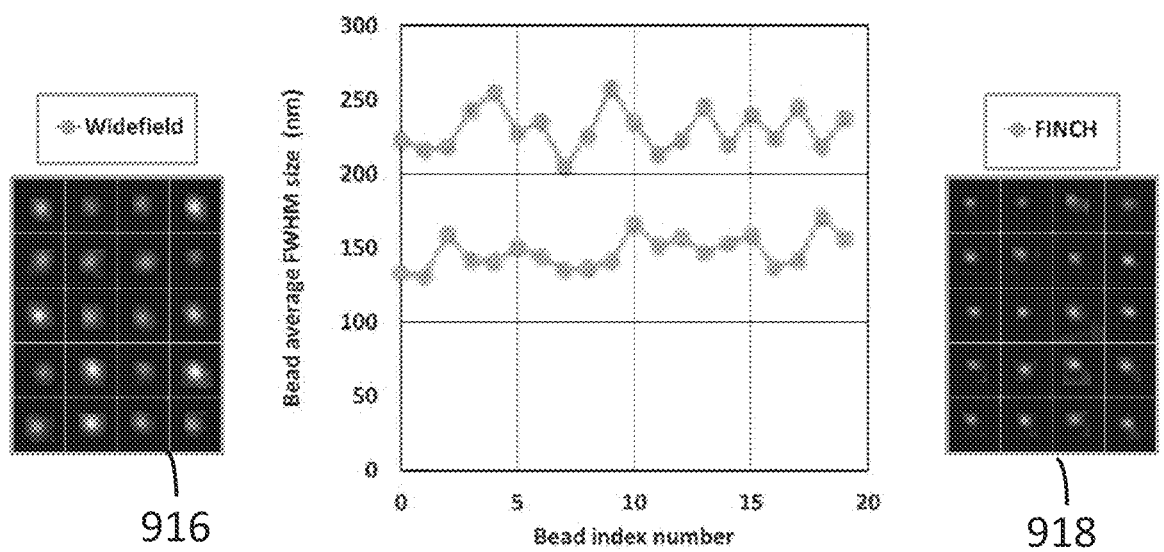
FIG. 9c. Comparative classical fluorescence microscopy and FINCH fluorescence microscopy of standard sub-resolution bead objects using a FINCH system incorporating a calcite BRL, according to one or more example embodiments, demonstrating improved image resolution in the FINCH image with a comparative plot of the widths of the bead intensity profiles measured by each method.
Figure 9D:
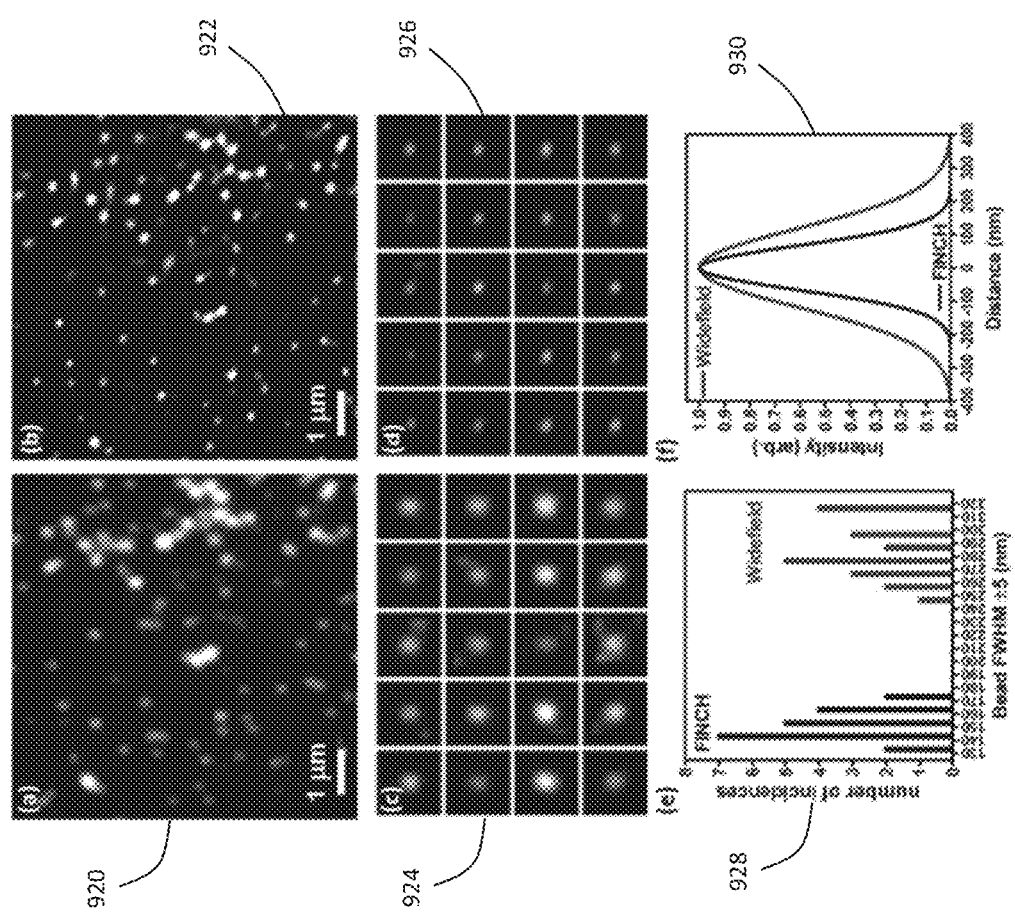
FIG. 9d. Comparative classical fluorescence microscopy and FINCH fluorescence microscopy of 110 nm bead objects using a FINCH system incorporating a single crystal α-BRL, according to one or more example embodiments, demonstrating improved image resolution in the FINCH image with a comparative plot of the widths of the bead intensity profiles measured by each method.

Birefringent spherical lenses made from alpha-barium borate ($\alpha$-BBO or alpha-BBO) were also used in some embodiments to create FINCH images of standard objects in fluorescence microscopy. Birefringent lenses and optical flats of calcite and of $\alpha$-BBO were made, according to an embodiment, by standard methods for fabrication of optical glass components, with their extraordinary axes lying in the plane orthogonal to the direction of light propagation through the optic. Birefringent optics may be made from $\alpha$-BBO because of its temperature and environmental stability as well as the property that it can be grown in large single crystals with high optical quality. In a microscope configured in a manner similar to FIG. 3, with a BBO lens and a separate BBO compensating flat replacing the active and inactive GRIN lenses 320 and 321, a fluorescent USAF test pattern and a sample of 100 nm diameter beads were imaged by both classical and FINCH imaging, the results of which are shown in FIG. 9b and FIG. 9c. FIG. 9b shows the results of classical imaging 912 and FINCH with BBO (e.g., $\alpha$-BBO) lens imaging 914. A 20×0.75 NA Nikon and a 60×1.49 NA Nikon TIRF objective lens were used, respectively, for the USAF pattern and the 100 nm beads. The wide-field and FINCH images of the 100 nm beads (590 nm wavelength) were deconvolved using a commercial application developed by Microvolution, Inc. Blind deconvolution was applied, using as the initial PSF guesses a classical PSF for the wide-field image and a custom PSF for the FINCH images. As shown in the images in FIG. 9b and FIG. 9c, the BBO-based FINCH imaging microscope was able to image an extended object at resolution comparable to that reported in the literature for a GRIN-based FINCH system. Furthermore, analysis of the images of 20 randomly selected bead images (shown in FIG. 9c for widefield 916 and BBO-based FINCH 918) from across the imaging plane show that the BBO-based FINCH system was able to resolve the beads at better than classical resolution limit, as predicted for FINCH imaging. In data not shown, a 100×1.4 NA Nikon objective was used to image a sample of FITC-stained microtubules, and the FINCH images of the microtubules showed cross sections of approximately 120 nm, further demonstrating the efficacy of the embodiment. FIG. 9d results, however, were obtained from $\alpha$-BBO-FINCH imaging of 110 nm sub-resolution fluorescent beads which require higher resolving power. 920 and 922 are 8×8 μm zoomed selections of 110 nm fluorescent beads for resolution comparison of the same area between 920 widefield fluorescence and 922 $\alpha$-BBO-FINCH images. 924 and 926 are 1 μm square zoomed images of the same randomly selected beads from 920 and 922 respectively. The beads in the respective parts of 924 and 926 are the same. A histogram 928 of FWHM size distributions amongst the 20 beads that were measured in 924 and 926, shows an approximately two-fold reduction in FWHM by FINCH. The plots 930 depict the average FWHM sizes of the 110 nm beads as measured by fluorescence and $\alpha$-BBO-FINCH microscopy, with normalized Gaussian functions of the average width measured from the 20 selected beads. When these beads were imaged with FINCH using a Nikon 60×1.49 NA TIRF objective (not in TIRF geometry), the $\alpha$-BBO-FINCH measurements of the bead sizes averaged 149±11 nm, significantly smaller than the 287±20 nm average from the corresponding classical images of the same exact beads. These results are comparable to beads imaged at a shorter wavelength by another super-resolution technique. To the inventors' knowledge these are the smallest objects that have been measured by any self-referenced holographic method, as well as the first demonstration of super-resolved self-referenced holographic imaging of any kind with a high magnification, high NA system. These advances are due to the high imaging quality of the birefringent lens incoherent interferometer based FINCH system of example embodiments. The development of the single crystal birefringent lens for FINCH holographic imaging enables FINCH to reach its full potential at the highest resolution and magnification and achieve the theoretically predicted super resolution not possible with other previously used hologram forming approaches. This is because of the common-path simplicity of the FINCH method and flexible, nonquantized polarization-based beamsplitting quality of the birefringent crystal lens approach that is not achievable with SLMs, currently available liquid crystal lenses or even dual beam-path interferometers that have also been used to generate self-referenced holograms. This achievement shows the potential of birefringent crystal lenses for use in other holographic and interferometric methods as well. For example these lens interferometers could simplify and stabilize the laser generated excitation beam in structured illumination or scanning holography as well as other incoherent interferometric applications.

Figure 10:
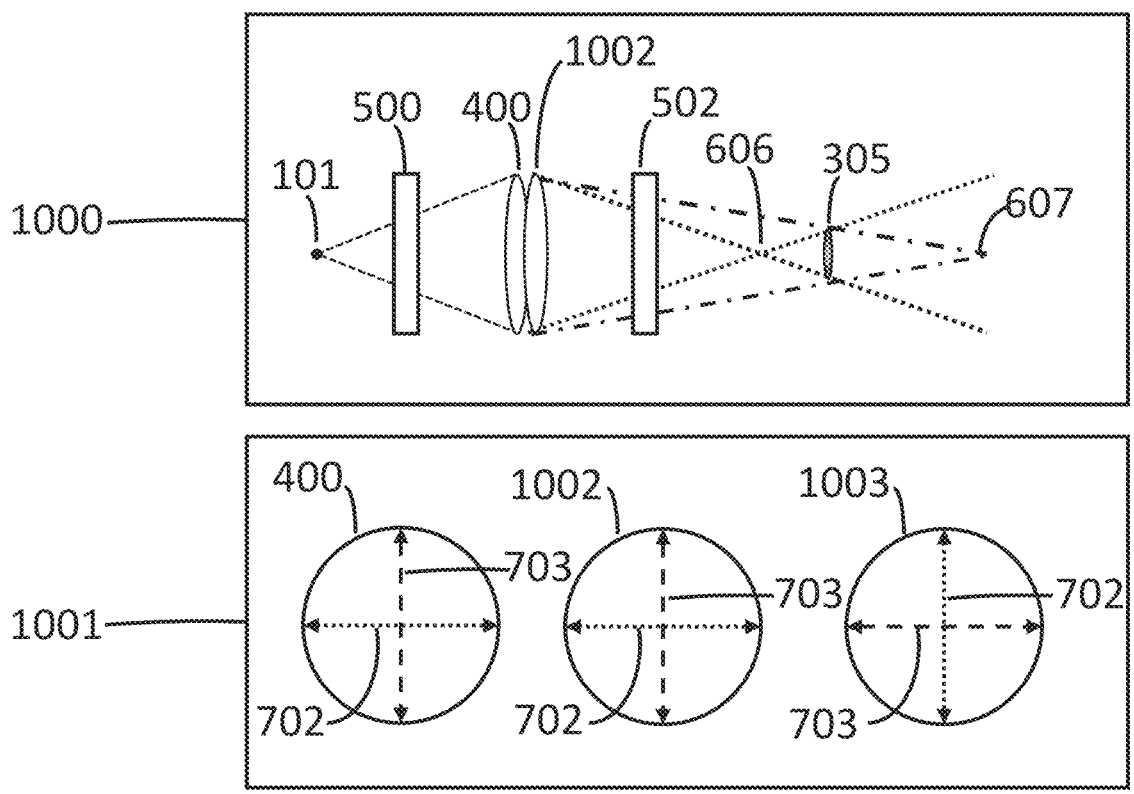
FIG. 10. A schematic of two birefringent lenses used in tandem, according to one or more example embodiments.

Other systems may be constructed that make use of BRLs. As shown in FIG. 10, another system 1000 incorporates two BRLs 400 and 1002 used together, whether said BRLs are made from the same material or not, to achieve further modification of the two waves. The cross section diagrams 1001 of the two BRLs show how a second BRL 1002 could be used, with its axes 702 and 703 parallel or perpendicular to the corresponding axes of the first BRL 400, to provide chromatic, spherical or other corrections to the first BRL.

Figure 11:
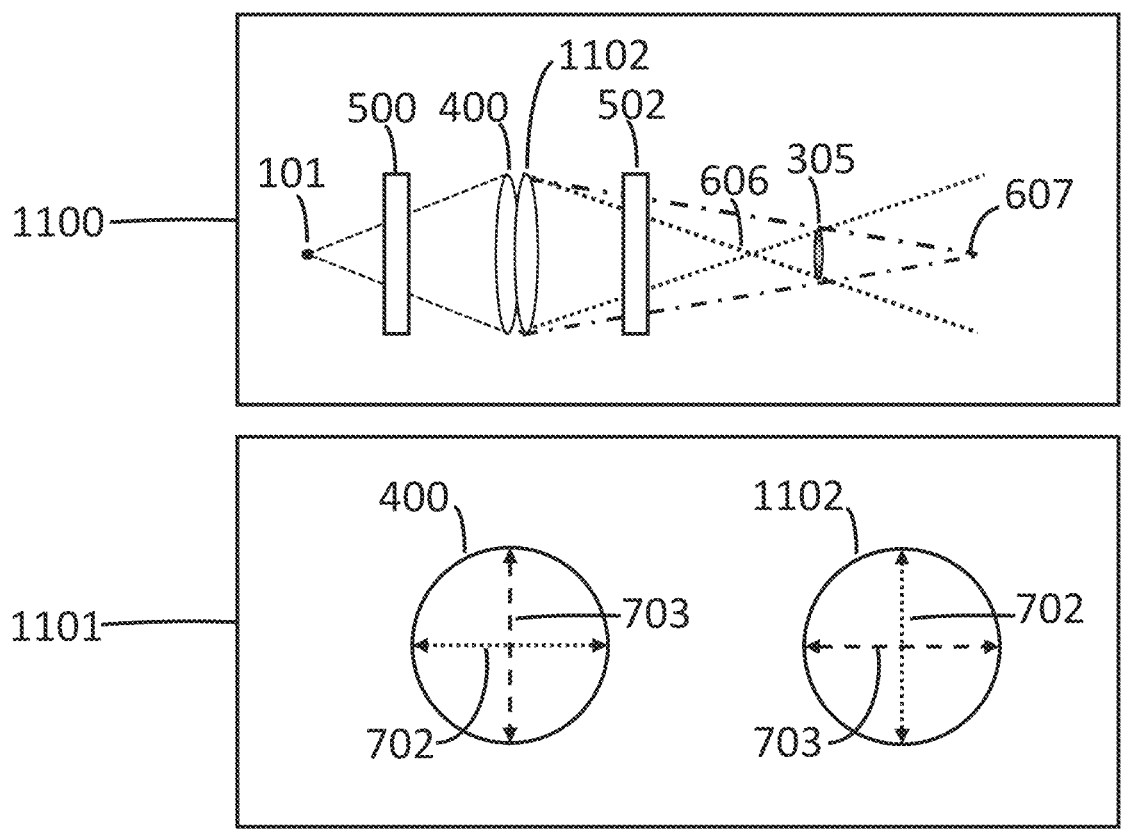
FIG. 11. A schematic of a birefringent lens used in conjunction with a flat birefringent plate, according to one or more example embodiments.

FIG. 11 shows another system 1100 incorporating a BRL with two flat sides, hereinafter called a birefringent flat (BRF) 1102, acting as a phase-delay compensating optic to change the total optical path difference between the two waves in addition to the BRL that differentially changes the spherical curvature of the wavefronts of the waves. The cross sections 1101 show the relative orientations of the ordinary and extraordinary refractive indices 702 and 703 of the BRL 400 and the BRF 1102. Optical path length (OPL) is a measure of the distance traveled by an EM wave, taking into account both the thicknesses of various media the waves traverse as well as their refractive indices:

$$OPL = \Sigma d_i n_i \quad (9)$$

where $d_i$ and $n_i$ are the thicknesses and refractive indices of all media in the path traveled by the wave. The optical path difference (OPD) of two waves is a measure of the difference in the OPLs the waves traveled. When dealing with incoherent holography, it is important to keep the total optical path difference between the two waves low in order to maintain the conditions necessary for holography interference to occur. The difference is required to be less than the coherence length of the light, which is generally approximated as $\lambda^2/\Delta\lambda$, where $\lambda$ is the center wavelength and $\Delta\lambda$ is the bandwidth. In the microscopy realm, the coherence length is on the order of 10 μm, at least an order of magnitude shorter than the lasers or monochromatic light to which previous interferometers with birefringent lenses have been restricted. The BRL not only imparts different curvatures to the two waves through the two focal lengths $f_{be}$ 606 and $f_{bo}$ 607, but also imparts an overall optical path difference $OPD_o$ between the two waves that is proportional to the thickness $d_{BRL}$ of the BRL and the two refractive indices of the birefringent material:

$$OPD_o = d_{BRL}(n_o - n_e) \quad (10)$$

Figure 13:
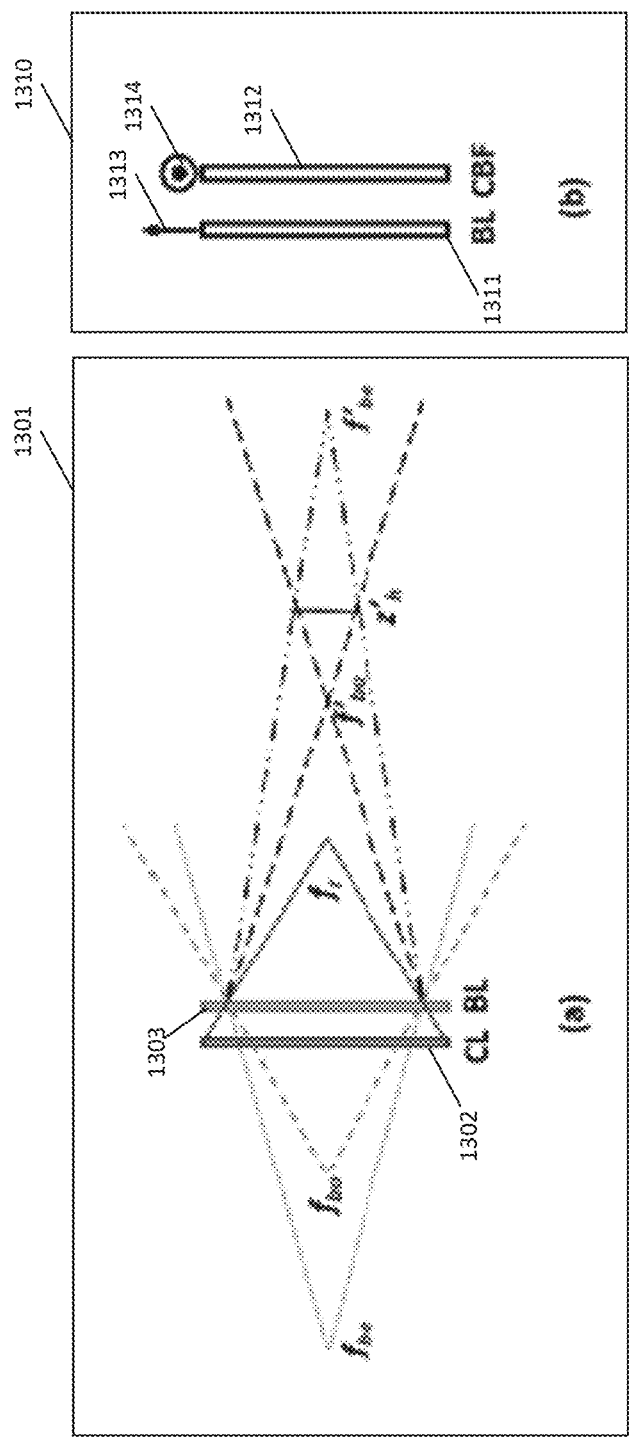
FIG. 13. Arrangements of optics in a birefringent lens incoherent interferometer in accordance with one or more example embodiments.

In any form of FINCH, the OPD between the two differentially focused beams has a geometric component due to the different physical paths that the light waves travel after exiting the differential focusing optic that is less than the coherence length and thus does not prevent the waves from interfering. For the GRIN method the birefringence $|\Delta n| = |n_o - n_e|$ of the liquid crystal material in the GRIN lens is enough to cause an additional large OPD component that is greater than the coherence length, which must be compensated for by another optic if interference is to be observed. A similar effect occurs in this case, in which the birefringent lens not only imparts different phase curvatures to the two waves through the two focal lengths $f_{be}$ and $f_{bo}$, related to the curved surfaces of the lens, but also imparts an overall optical path difference $\Delta OPD$ between the two waves that is proportional to the thickness $d_{BRL}$ of the central cross-sectional part of the birefringent lens as in equation (10). This $\Delta OPD$ does not contribute to the desired geometric optical path difference, as there is no physical curvature in this part of the lens, and for a birefringent lens with thickness >1 mm and $\Delta n$ approximately 0.1 it is far greater than the 10 μm coherence length and is thus sufficient to prevent interference from occurring. A correction similar to the GRIN method is made here, in which a compensating birefringent optical flat of thickness equal to the center thickness of the birefringent lens and cut with the same orientation of its crystal axes is placed in the optical train with its extraordinary axis rotated by 90° in the transverse plane relative to the extraordinary axis of the birefringent lens (e.g., as shown in FIG. 13). The wave that projects along the ordinary axis in the birefringent lens projects along the extraordinary axis of the compensating birefringent flat, and vice versa, so the non-spherical $\Delta OPD$ from the birefringent lens is canceled by the compensating birefringent flat.

By using a BRF of the same thickness and cutting angle as the BRL, but rotated by 90 degrees in the plane orthogonal to the direction of EM propagation, the $OPD_o$ may be corrected without changing the relative difference in the spherical curvatures of the two waves. The wave that projects along the ordinary axis in the BRL projects along the extraordinary axis of the BRF, and vice versa, so the non-spherical $OPD_o$ from the BRL is canceled by the BRF. Tilting the BRF slightly changes the magnitude of this OPD matching effect to achieve maximum interference contrast.

Figure 12:
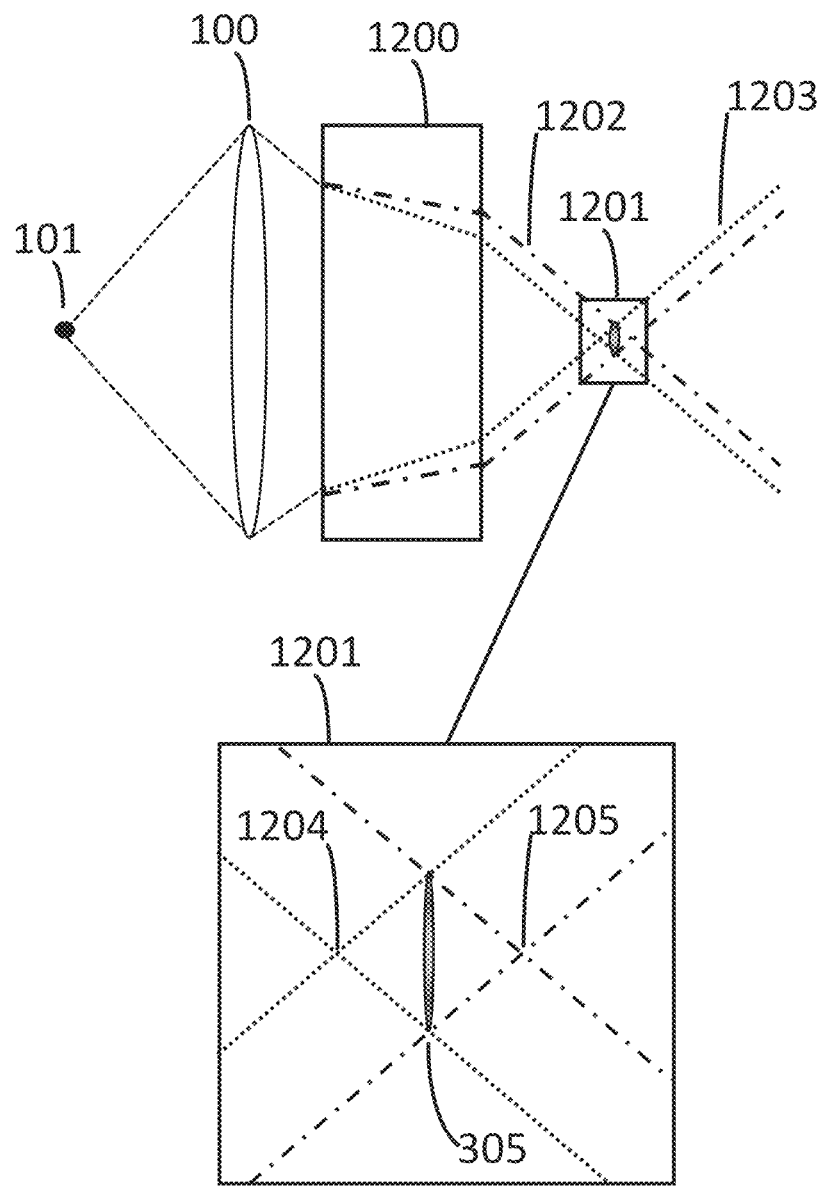
FIG. 12. A schematic of a birefringent plate or block used to create two focal planes from a single spherical glass lens, according to one or more example embodiments.

Another system shown in FIG. 12 incorporates only a BRF 1200 along with a glass lens 100 to effect the separation of the received wave from the object 101 into two waves. Waves with positive spherical curvature entering a medium experience a delay in achieving their focal point. This delay $\Delta$ is proportional to the thickness t and refractive index n of the medium:

$$\Delta = t\left(1 - \frac{1}{n}\right) \quad (11)$$

It can readily be seen in the magnified part 1201 of FIG. 12 that a BRF can delay the wave 1202 parallel to the ordinary axis and the wave 1203 parallel to the extraordinary axis by different amounts due to the differing refractive indices, which separates the focal planes 1204 and 1205 of the two waves and allows for holography interference 305 to take place.

Some example embodiments use thin birefringent lenses in conjunction with classical refractive lenses in order to achieve a compound birefringent lens system (CBLS) that splits the received electromagnetic radiation into two differentially phase-modulated components parallel to the extraordinary and ordinary axes of the birefringent lens, that propagate along the optical axis. A "thin birefringent lens", as used in this disclosure, is a birefringent lens having a thickness (e.g., in the thickest section) that is less than or equal to 15% of its diameter. In some embodiments, the thin birefringent lenses have a thickness that is 10% or less than the diameter. Thin birefringent lenses having a thickness that is 15% or less of the diameter are used as a close approximation of an idealized thin lens. In light of the fact that birefringent lenses made from birefringent single crystals may be difficult and expensive to produce, it is notable that the deficiencies of other BRL types may be attenuated by judicious combination with classical lenses. In this way, it may be considered that the bulk of the focal power originates in the classical component of a CBLS, while the birefringent component contributes just enough differential phase modulation (e.g., approximately 5%; a 5% difference contributes approximately 3-10% differential phase modulation) to produce the hologram interference with minimal amounts of overall aberration.

Birefringent components that are applicable to this concept include birefringent Fresnel lenses made with either solid or liquid crystalline material, other optical elements made with patterned birefringent solid or liquid crystalline material, and micro- or nano-structured metamaterial optical elements; all of which will be referred to herein as thin birefringent components (TBCs). Micro- or nano-structure optical elements can include structures made of patterned silicon dioxide or other materials in which the patterns consist of nano-structures with defined periodic radii, shapes and/or orientations that combine to produce a focusing effect. Arbabi, A. et al. *Subwavelength-thick lenses with high numerical apertures and large efficiency based on high-contrast transmit arrays*, Nat. Commun. 6:7069 doi: 10.1038/ncomms8069 (2015), which is incorporated herein in its entirety, describes micro- and nano-structures. The notable potential advantages of TBCs include (1) very low (e.g., 0 or substantially 0) overall phase shift $OPD_0$ of the sort described earlier in equation 10, (2) very low (e.g., 0 or substantially 0) spherical aberration due to their near planar structure and (3) the opportunity to encode other phase patterns besides spherical quadratic patterns into the TBC for the purposes of optimizing the system for a given use or to correct for aberrations from other components in the system.

Potential disadvantages of TBC's arise from their natures as diffractive lenses. Lenses made from TBCs (e.g., Fresnel lenses, lenses with micro- or nano-structures) generally have large chromatic shifts of focal length, which would have the undesirable effect of spreading the optimal hologram plane $z_h$ over a large area of three-dimensional space in a system with any wavelength bandwidth; and TBC-lenses also impart phase aberrations such as diffraction rings and higher-order diffraction components to transmitted beams. However, in the limit of TBC-lenses with long focal lengths, these disadvantages may be mostly or entirely negated for the purposes of FINCH or other holography by combining them with classical lenses in CBLSs.

The chromatic variation in focal length for diffractive lenses is generally approximated as $$\frac{\Delta f}{f} = \frac{\Delta \lambda}{\lambda} \tag{12}$$

where f and λ are focal length and wavelength, respectively. However the Abbe number for diffractive lenses is −3.45, in distinction to those refractive lenses for which it is positive and of larger magnitude. Thus, while a TBC of 300 mm nominal focal length will have a focal length spread out over about 20 mm along the optical axis for a standard 40 nm microscope bandwidth, for example, a TBC with a focal length of several thousand mm (e.g., 5000 mm or approximately 5000 mm) can be coupled with a 300 mm (or approximately 300 mm) focal length classical lens to achieve a CBLS with much lower chromatic dispersion. This relationship follows from the achromatic lens formula in equation 13a (of the sum to be minimized to achieve achromatic correction in a two-lens system) and its logical consequence in equation 13b (for the value of the focal length $f_2$ that achieves best achromatic correction for a given pair of lenses):

$$\min(f_1 v_{d1} + f_2 v_{d2}) \tag{13a}$$

$$f_1 = -\left(\frac{f_1 v_{d1}}{v_{d2}}\right) \tag{13b}$$

in which $v_d$ is the Abbe number. The tables below show example systems that compare a single diffractive lens to a CBLS system that combined a long focal length (e.g., 5000 mm or approximately 5000 mm) diffractive lens with a short focal length (e.g., 300 mm or approximately 300 mm) refractive lens. The chromatic shift in total focal length is much lower for the CBLS system, which will enable much better holographic performance.

TABLE 2 chromatic dispersion of focal length of a diffractive lens

| λ (nm) actual | λ (nm) nominal | Δλ (nm) | Diffractive lens nominal f (mm) | Δf (mm) | Diffractive lens actual f (mm) |
|---|---|---|---|---|---|
| 570 | 590 | 20 | 300 | 10.17 | 310.17 |
| 580 | 590 | 10 | 300 | 5.08 | 305.08 |
| 590 | 590 | 0 | 300 | 0.00 | 300.00 |
| 600 | 590 | −10 | 300 | −5.08 | 294.92 |
| 610 | 590 | −20 | 300 | −10.17 | 289.83 |

Legend:
λ and f are light wavelength and lens focal length, respectively.
Δλ is the difference between the actual wavelength and the nominal wavelength for which the diffractive lens is designed for.
Δf is the change in diffractive lens focal length resulting from the wavelength change.
Diffractive lens actual f is the actual focal length at the specified actual wavelength.

TABLE 3 combined focal lengths of diffractive lens and classical lens

| λ (nm) actual | λ (nm) nominal | Δλ (nm) | Diffractive lens nominal f (mm) | Δf (mm) | Diffractive lens actual f (mm) | classical lens approximate f (mm) | Actual combined f (mm) |
|---|---|---|---|---|---|---|---|
| 570 | 590 | 20 | 5000 | 169.49 | 5169.49 | 300 | 283.55 |
| 580 | 590 | 10 | 5000 | 84.75 | 5084.75 | 300 | 283.29 |
| 590 | 590 | 0 | 5000 | 0.00 | 5000.00 | 300 | 283.02 |
| 600 | 590 | −10 | 5000 | −84.75 | 4915.25 | 300 | 282.74 |
| 610 | 590 | −20 | 5000 | −169.49 | 4830.51 | 300 | 282.46 |

Legend:
λ and f are light wavelength and lens focal length, respectively.
Δλ is the difference between the actual wavelength and the nominal wavelength for which the diffractive lens is designed for.
Δf is the change in diffractive lens focal length resulting from the wavelength change. Diffractive lens actual f is the actual focal length at the specified actual wavelength. Actual combined f is the combined focal length of the classical and diffractive lens calculated by the thin lens approximation and assuming no distance between the lenses.

From the above tables and equations, it can readily be seen that combining a classical lens with a TBC lens possessing one or two polarization-dependent focal lengths can result in a CBLS with the two differentially focused or phase modulated electromagnetic beams necessary for FINCH or other holography, with relatively little (e.g. less than 2 mm) chromatic dispersion of the focal planes of each beam, and therefore with hologram distance $z_h$ that is sharply defined and allows for high fringe contrast in the interference of the beams. It is also noted that following equations 7 and 8, a CBLS designed on these principles will also have significant potential flexibility in choice of spacing factor s and hologram distance $z_h$.

Furthermore, the diffractive aberrations introduced by TBCs derive from the sharp phase-transition regions or discontinuities in the component's phase profile, such as the phase wrapping points of a Fresnel or other TBC lens. With fewer phase wrapping regions, then, the number of phase aberrations should be reduced. Since the number of phase wrapping regions is directly proportional to the focal length of a TBC lens, there will be very few phase wrapping regions in the limit of long focal length, and correspondingly fewer aberrations introduced. In the very long focal length limit (e.g., in the limiting case where the focal length of the lens requires less than one wave of phase shift between the center and edge of the lens, no phase wrapping regions occur), there might be no phase wrapping regions at all, and the system might be treated as a fully refractive one.

FIG. 13 shows various arrangements of optics in a birefringent lens incoherent interferometer according to some example embodiments. In (a) 1301, the combination of a classical lens (CL) 1302 (in this case convergent) with a birefringent lens (BL) 1303 (in this case negative) to produce combined focal planes and hologram plane as in the text in equations 7 and 8b. Note that other combinations are possible as well. In (b) 1310, the combination of a birefringent lens (BL) 1311 with a birefringent compensating flat (CBF) 1312 to reduce the overall optical path difference encountered by the light propagating through the interferometer is shown. The orientations of the extraordinary axes of the birefringent lens and the compensating flat are indicated by the arrow 1313 and target 1314, representing in the plane of the paper and orthogonal to it, respectively.

Figure 14:
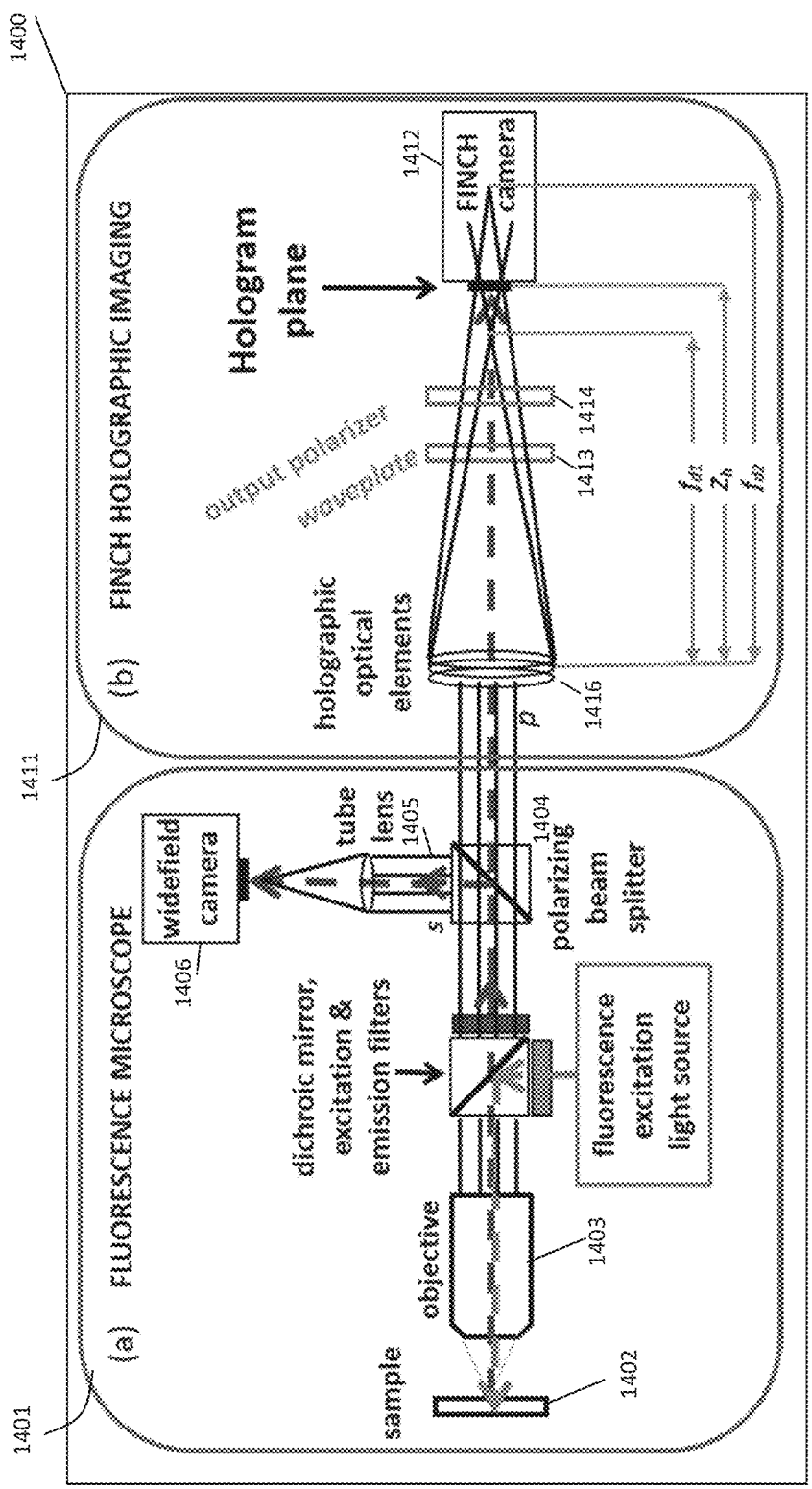
FIG. 14. Schematic illustration of a FINCH microscope according to some example embodiments

FIG. 14 schematically illustrates a FINCH microscope 1400 according to some example embodiments. In (a) 1401, a standard fluorescent microscope arrangement in which fluorescent light emitted from a sample 1402 in the microscope is shown. The fluorescent light emitted from the sample passes through an infinity corrected objective 1403, after which point it is split by a beam splitter 1404 into two polarized beams. The s polarization is directed through a microscope tube lens 1405 and the image is captured on the widefield camera 1406 as in a classical microscope. In (b) 1411, beam splitting into two orthogonally polarized beams typical of a FINCH hologram forming system configured with SLM based or GRIN lens based or a birefringent crystal lens based interferometer is shown. The emitted light propagates through the objective and a polarizing beamsplitter to an optical train that applies different spherical phases (focusing power) to different polarization components of the light beam, creating a pair of co-propagating differentially focused beams with focal lengths fd1 and fd2. The beams propagate until their interference is recorded at the ideal hologram plane located at distance zh. Following the recording of a set of holograms used to recreate the complex field at the recording plane, a final processed image is calculated by Fresnel propagation and a subsequent deconvolution. The p polarization is directed through holographic optical elements 1416 which create holograms that are captured on the FINCH camera 1412. The phase of the hologram can be changed by an optional polarization sensitive variable waveplate 1413 if the phase shifting holographic method is used. Additional contrast can also be obtained by inclusion of an optional output polarizer 1414. Not shown for simplicity is a 4F relay system between (a) 1401 and (b) 1411.

Uniaxial birefringent α-BBO and calcite crystal materials were used in example embodiments to create lens based in line incoherent interferometers. These common path incoherent interferometers allowed the inventors to make for the first time a FINCH holographic super resolution microscope with high magnification/numerical aperture objectives. Birefringent crystal lens incoherent interferometers utilize non quantized refractive lenses that create higher quality FINCH holograms because they are free of quantization errors and aberrations inherent in SLM or GRIN lens devices used to produce FINCH holograms. A simple fluorescence microscope incorporating these new birefringent lens interferometers has a lateral point spread function (PSF) width of 149 nm at 590 nm center wavelength with a 60×1.49 NA objective. This is a significant improvement beyond the resolution of standard widefield fluorescence microscopes and experimentally achieves sub diffraction super resolution performance predicted for FINCH fluorescence microscopy. Birefringent incoherent crystal interferometers are contemplated in embodiments to aid other holographic applications.

Another use for a birefringent lens common path interferometer based on these design principles is in the creation of the excitation beam in optical scanning holography (OSH) and particularly in scanning holographic microscopy [J, Opt. Soc. Am. A 22, 892-898 (2005)]. The excitation beam in OSH microscopy is created by interfering two beams that are coherent with each other at the back focal plane of an objective lens, resulting in the formation of an interferogram that is identical to a Fresnel complex hologram. This excitation interferogram is then focused into the sample to produce a small excitation spot. Since the process of forming the excitation interferogram is identical in principle to the formation of a FINCH hologram, it is clear that current methods for forming the excitation Hologram suffers from the same drawbacks as many other hologram methods that FINCH was designed to remedy. Therefore a common-path birefringent interferometer should provide the same advantages to the excitation interferogram in OSH as in FINCH, including ease and stability of alignment, and elimination of sensitivity to environmental vibrations. Furthermore, given that both OSH microscopy [J. OpL Soc. Am. A 22, 892-898 (2005)] and FINCH (as noted above) are independently capable of super-resolution by factors of up to 2 when compared to classical imaging methods, it is possible to combine scanning OSH excitation with FINCH imaging detection to achieve even further increases in super-resolution, potentially up to a factor of 4 compared to classical imaging. Additionally, it may be possible to use the same birefringent interferometer to produce both the excitation interferogram and the emission FINCH hologram, simplifying and stabilizing a joint OSH/FINCH system even further.

Numerous modifications and variations of the present invention are possible in light of the above teachings. It is therefore to be understood that within the scope of the appended claims, the invention may be practiced otherwise than as specifically described herein.

What is claimed is:

1. An optical apparatus, comprising:
a plurality of lenses including at least one thin birefringent lens, wherein the plurality of lenses are configured to:
receive electromagnetic radiation from an object, wherein the electromagnetic radiation is incoherent light;
transform, by transmission using the at least one thin birefringent lens in an electrically independent manner, the received electromagnetic radiation to generate two or more differentially modulated electromagnetic waves propagating in a common path, wherein the transformation does not include an overall phase delay between the differentially modulated waves beyond that necessary to generate discrete modulated waves; and
provide for the differentially modulated electromagnetic waves to create electromagnetic interference, without the use of phase compensating optics to correct for an undesired phase delay.

2. The optical apparatus according to claim 1, wherein the at least one thin birefringent lens includes one of a birefringent Fresnel lens made with solid crystalline material, or a birefringent Fresnel lens made with liquid crystalline material.

3. The optical apparatus according to claim 1, wherein the at least one thin birefringent lens includes a patterned birefringent solid or liquid crystalline material.

4. The optical apparatus according to claim 1, wherein the at least one thin birefringent lens includes a nano-structured non-birefringent material, wherein the birefringent properties are imparted by patterns encoded in the nano-structures.

5. The optical apparatus according to claim 4, wherein the at least one thin birefringent lens encodes one or more spherical quadratic phase patterns.

6. The optical apparatus according to claim 4, wherein the at least one thin birefringent lens further encodes one or more phase patterns other than spherical quadratic phase patterns.

7. The optical apparatus according to claim 1, wherein the at least one thin birefringent lens encodes spherical quadratic phase patterns.

8. The optical apparatus according to claim 7, wherein the at least one thin birefringent lens further encodes phase patterns other than spherical quadratic phase patterns.

9. The optical apparatus according to claim 1, wherein the at least one thin birefringent lens has a near planar structure.

10. The optical apparatus according to claim 1, wherein at least one classical lens of the plurality of lenses is located proximally to the at least one thin birefringent lens and is configured to compensate, by wavelength dependent focusing only, for the chromatic shifts caused by the at least one thin birefringent lens to reduce spreading of an optimal hologram plane.

11. The optical apparatus according to claim 10, wherein a focal length of the at least one thin birefringent lens is greater than a focal length of the at least one classical lens located proximally to the at least one thin birefringent lens.

12. The optical apparatus according to claim 11, wherein the at least one thin birefringent lens has a focal length greater than 1000 mm and the at least one classical lens has a focal length of 300 mm, and wherein the plurality of lenses have a combined focal length spread out over less than 20 mm along an optical axis for a 40 mm microscope bandwidth.

13. The optical apparatus according to claim 10, wherein the at least one thin birefringent lens has two polarization-dependent focal lengths.

14. The optical apparatus according to claim 13, wherein the plurality of lenses have one or more of configurable spacing factor or hologram distance, wherein the configurability is provided by the selection of the focal lengths, curvatures and respective distances of each of the plurality of the lenses.

15. The optical apparatus of claim 1, further comprising a scanning holographic microscope, wherein the created electromagnetic interference is provided to the scanning holographic microscope as an excitation beam for optical scanning holography.

16. The optical apparatus of claim 1, wherein the optical apparatus includes a microscope.

17. The optical apparatus of claim 16, wherein the optical apparatus includes a microscope for ophthalmological fundus applications.

18. The optical apparatus of claim 16, wherein the microscope is any of a reflection microscope, or a fluorescent microscope.

19. The optical apparatus of claim 1, wherein the at least one thin birefringent lens includes an alpha-BBO lens.

20. The optical apparatus of claim 19, wherein the alpha-BBO lens is a single crystal alpha-BBO lens.

21. A method, comprising:
receiving, in a plurality of lenses including at least one thin birefringent lens, electromagnetic radiation from an object, wherein the received electromagnetic radiation is incoherent light;
transforming, by transmission using the at least one thin birefringent lens in an electrically independent manner, the received electromagnetic radiation to generate two or more differentially modulated electromagnetic waves propagating in a common path, wherein the transforming does not include an overall phase delay between the differentially modulated waves beyond that necessary to generate discrete modulated waves; and
providing for the differentially modulated electromagnetic waves to create electromagnetic interference, without the use of phase compensating optics to correct for an undesired phase delay.

22. The method according to claim 21, wherein the at least one thin birefringent lens includes one of a birefringent Fresnel lens made with solid crystalline material, or a birefringent Fresnel lens made with liquid crystalline material.

23. The method according to claim 21, wherein the at least one thin birefringent lens includes a patterned birefringent solid or liquid crystalline material.

24. The method according to claim 21, wherein the at least one thin birefringent lens includes a nano-structured non-birefringent material, wherein the birefringent properties are imparted by patterns encoded in the nano-structures.

25. The method of claim 21, further comprising providing the created electromagnetic interference to a scanning holographic microscope as an excitation beam for optical scanning holography.

* * * * *

UNITED STATES PATENT AND TRADEMARK OFFICE
CERTIFICATE OF CORRECTION

PATENT NO.        : 10,591,870 B2
APPLICATION NO.   : 15/588096
DATED             : March 17, 2020
INVENTOR(S)       : Gary Brooker et al.

It is certified that error appears in the above-identified patent and that said Letters Patent is hereby corrected as shown below:

In the Specification

On Column 1, Lines 32-37, replace with the following:
This invention was made with U.S. government support under grant R44CA192299 awarded by the National Institutes of Health. The U.S. government has certain rights in the invention.

Signed and Sealed this
Twenty-ninth Day of August, 2023

*Katherine Kelly Vidal*

Katherine Kelly Vidal
*Director of the United States Patent and Trademark Office*